United States Patent
Sada

(10) Patent No.: US 11,369,112 B2
(45) Date of Patent: Jun. 28, 2022

(54) METHOD FOR CONTROLLING PESTS OF FARM CROPS

(71) Applicant: Sumitomo Chemical Company, Limited, Tokyo (JP)

(72) Inventor: Yoshinao Sada, Kasai (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 7 days.

(21) Appl. No.: 16/814,421

(22) Filed: Mar. 10, 2020

(65) Prior Publication Data

US 2020/0205409 A1 Jul. 2, 2020

Related U.S. Application Data

(63) Continuation of application No. 16/256,350, filed on Jan. 24, 2019, now abandoned, which is a continuation of application No. PCT/JP2017/026634, filed on Jul. 24, 2017.

(30) Foreign Application Priority Data

Jul. 29, 2016 (JP) .............................. JP2016-149454
Sep. 7, 2016 (JP) .............................. JP2016-174382

(51) Int. Cl.
*A01N 25/04* (2006.01)
*A01N 43/54* (2006.01)
*C07D 401/12* (2006.01)

(52) U.S. Cl.
CPC ........... *A01N 43/54* (2013.01); *C07D 401/12* (2013.01); *A01N 25/04* (2013.01)

(58) Field of Classification Search
None
See application file for complete search history.

(56) References Cited

U.S. PATENT DOCUMENTS

| | | | | |
|---|---|---|---|---|
| 6,537,948 | B1 ‡ | 3/2003 | Tohyama et al. .... | C07D 213/69 504/24 |
| 7,485,601 | B2 * | 2/2009 | Nishio .................. | A01N 47/36 504/136 |
| 2009/0233796 | A1 ‡ | 9/2009 | North ................. | A01N 2300/00 504/24 |
| 2019/0142005 | A1 | 5/2019 | Sada | |
| 2019/0166838 | A1 | 6/2019 | Armel et al. | |

FOREIGN PATENT DOCUMENTS

| | | |
|---|---|---|
| EP | 1122244 A1 | 8/2001 |
| EP | 1397958 A1 | 3/2004 |
| EP | 1470753 A1 | 10/2004 |
| JP | 2002-155061 A | 5/2002 |
| JP | 2008-522965 A | 7/2008 |
| JP | 2015-166386 A | 9/2015 |
| WO | 2007014758 A1 | 2/2007 |
| WO | WO 2018/016641 A1 | 1/2018 |

OTHER PUBLICATIONS

Flumioxazin | CAS#: 103361-09-7 | Chemsrc, 1997 (Year: 1997).*
Australian Office Action dated Apr. 23, 2021 in Australian Patent Application No. 2017301293, 6 pages.
Compendium of Pesticide Common Names, Wood, downloaded from web page: http://www.alanwood.net/pesticides/ Download date: Apr. 2019, original posting date: unknown, 2 pages.
Int'l Preliminary Report on Patentability dated Oct. 24, 2017 in Int'l Application No. PCT/JP2017/026634 (English-language translation).
Int'l Search Report dated Oct. 24, 2017 in Int'l Application No. PCT/JP2017/026634.
Anon, "SYN 523 (S-3100)", AgroIP, (Jan. 2012).
Bond et al., "Managing PPO-resistant Palmer Amaranth in Mississippi Soybean", Allegro, 4 pages, (Mar. 2016).
Steckel, "PPO-Resistant Palmer Amaranth escaping Sharpen Burndown", UTcrops News Blog, (Jun. 2016).
U.S. Patent and Trademark Office (USPTO) Office Action dated Dec. 11, 2019 in U.S. Appl. No. 16/256,350.
Australian Office Action dated Sep. 17, 2021 in Patent Application No. 2017301293, 3 pages.
Office Action dated Mar. 21, 2022 in the corresponding Argentina application No. 20170102121 (with English Translation), 9 pages.

* cited by examiner
‡ imported from a related application

*Primary Examiner* — Alton N Pryor
(74) *Attorney, Agent, or Firm* — Oblon, McClelland, Maier & Neustadt, L.L.P.

(57) ABSTRACT

Provided is a method for controlling harmful organisms in a cultivation area of crops, including the steps of: (1) treating crop seeds with one or more fungicidal and/or plant growth regulator compounds; (2) treating a cultivation area of crops with ethyl [3-[2-chloro -4-fluoro-5-(1-methyl-6-trifluoromethyl-2,4-dioxo-1,2,3,4 -tetrahydropyrimidin-3-yl)phenoxy]-2-pyridyloxy]acetate before, simultaneously with, and/or after sowing the crop seeds; and (3) performing a foliage treatment on crops with one or more compounds, which may include fungicidal and/or insecticidal compound(s), during a growing period of the crops, which has an excellent efficacy for controlling harmful organisms in a cultivation area of crops.

2 Claims, No Drawings

METHOD FOR CONTROLLING PESTS OF FARM CROPS

CROSS-REFERENCE TO RELATED APPLICATIONS

This application is a Continuation of U.S. patent application Ser. No. 16/256,350, filed Jan. 24, 2019, which is a Continuation of International Application No. PCT/JP2017/026634, filed Jul. 24, 2017, which was published in the Japanese language on Feb. 1, 2018, under International Publication No. WO 2018/021218 A1, which claims priority under 35 U.S.C. § 119(b) to Japanese Application No. 2016-149454, filed Jul. 29, 2016 and Japanese Application No. 2016-174382, filed Sep. 7, 2016, the disclosures of which are incorporated herein by reference in their entirety.

TECHNICAL FIELD

The present invention relates to a method for controlling harmful organisms in crops, in other words, harmful arthropods, nematodes, plant pathogens, and/or weeds and a herbicidal composition.

BACKGROUND ART

Various compounds are known as active ingredients of an insecticide, a nematicide, or a fungicide. Further, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate is known as an active component of a herbicide (see Patent Document 1 and Non-Patent Document 1).

RELATED ART DOCUMENT

Patent Document

[Patent Document 1] U.S. Pat. No. 6,537,948

Non-Patent Document

[Non-Patent Document 1] Compendium of Pesticide Common Names (http://www.alanwood.net/pesticides/)

SUMMARY OF THE INVENTION

Problems to be Solved by Invention

An object of the present invention is to provide an excellently effective method for controlling harmful organisms in a cultivation area of crops.

Means to Solve Problems

The present invention relates to a method for controlling weeds by treating a cultivation area of crops with ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate before, simultaneously with, and/or after sowing crop seeds; and a method for controlling harmful organisms generated in a cultivation area by treating a cultivation area of crops with ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate before, simultaneously with, and/or after sowing the crop seeds treated with one or more compounds selected from the group consisting of an insecticidal compound, a nematicidal compound, and a fungicidal compound and the like, and by combining a foliage treatment of one or more compounds selected from the group consisting of an insecticidal compound, a nematicidal compound, a fungicidal compound, and a herbicidal compound and the like.

The present invention includes the followings.

[1] A method for controlling weeds, comprising a step of treating a cultivation area of crops with ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate before, simultaneously with, and/or after sowing crop seeds.

[2] A method for controlling harmful organisms in a cultivation area of crops, comprising the steps of: (1) treating crop seeds with one or more compounds selected from compound group A; (2) treating a cultivation area of crops with ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate before, simultaneously with, and/or after sowing the crop seeds obtained by the above step; and (3) performing a foliage treatment on crops with one or more compounds selected from compound group B during a growing period of the crops, Compound group A: the group consisting of a neonicotinoid compound, a diamide compound, a carbamate compound, an organic phosphorus compound, a biological nematicidal compound, other insecticidal compounds and nematicidal compounds, an azole compound, a strobilurin compound, a metalaxyl compound, an SDHI compound, and other fungicidal compounds and plant growth regulators, Compound group B: the group consisting of a strobilurin compound, an azole compound, an SDHI compound, other fungicidal compounds, a pyrethroid compound, a benzoylphenylurea compound, an organic phosphorus insecticidal compound, a neonicotinoid compound, and a diamide compound.

[3] The control method according to [2], wherein one or more compounds selected from the compound group A is one or more compounds selected from the group consisting of the following compounds, Neonicotinoid compounds: clothianidin, thiamethoxam, imidacloprid, dinotefuran, nitenpyram, triflumezopyrim, dicloromezotiaz, sulfoxaflor, flupyradifurone, acetamiprid, and thiacloprid;

Diamide compounds: flubendiamide, chlorantraniliprole, cyantraniliprole, cyclaniliprole, broflanilide, cyhalodiamide, and tetraniliprole;

Carbamate compounds: aldicarb, oxamyl, thiodicarb, carbofuran, carbosulfan, and dimethoate;

Organic phosphorus compounds: fenamiphos, imicyafos, fensulfothion, terbufos, fosthiazate, phosphocarb, dichlofenthion, isamidofos, isazophos, ethoprophos, cadusafos, chlorpyrifos, heterofos, mecarphon, phorate, thionazin, triazophos, diamidafos, fosthietan, and phosphamidon;

Biological nematicidal compounds: Harpin Protein, *Pasteuria nishizawae, Pasteuria penetrans, Pasteuria usage, Myrothecium verrucaria, Burkholderia cepacia, Bacillus chitonosporus, Paecilomyces lilacinus, Bacillus amyloliguefaciens, Bacillus firmus, Bacillus subtilis, Bacillus pumulus, Trichoderma harzianum, Hirsutella rhossiliensis, Hirsutella minnesotensis, Verticillium chlamydosporum*, and *Arthrobotrys dactyloides*;

Other insecticidal compounds and nematicidal compounds: fipronil, ethiprole, beta-cyfluthrin, tefluthrin, chlorpyrifos, abamectin, spirotetramat, tioxazafen, fluazaindolizine, fluensulfone, and fluxametamide;

Azole compounds: azaconazole, bitertanol, bromuconazole, cyproconazole, difenoconazole, diniconazole, epoxyconazole, fenbuconazole, fluquinconazole, flusilazole, flutriafol, hexaconazole, imibenconazole, ipconazole, metconazole, myclobutanil, penconazole, propiconazole, prothioconazole, simeconazole, tebuconazole, tetraconazole, triadimenol, triticonazole, fenarimol, nuarimol, pyrifenox, imazalil, oxpoconazole fumarate, pefurazoate, prochloraz, triflumizole, ipfentrifluconazole, and mefentrifluconazole;

Strobilurin compounds: kresoxim-methyl, azoxystrobin, trifloxystrobin, fluoxastrobin, picoxystrobin, pyraclostrobin, dimoxystrobin, pyribencarb, metominostrobin, orysastrobin, and mandestrobin;

Metalaxyl compounds: metalaxyl and metalaxyl-M;

SDHI compounds: sedaxane, penflufen, carboxin, boscalid, furametpyr, flutolanil, fluxapyroxad, isopyrazam, fluopyram, tifluzamide, isofetamid, pyraziflumid, pydiflumetofen, N-(7-fluoro-1,1,3-trimethylindan-4-yl)-1-methyl-3-difluoromethylpyrazole-4-carboxamide (including a racemate or an enantiomer and a mixture of an R enantiomer and an S enantiomer at any mixing ratio), and N-(1,1,3-trimethylindan-4-yl)-1-methyl-3-difluoromethylpyrazole-4-carboxamide (including a racemate or an enantiomer and a mixture of an R enantiomer and an S enantiomer at any mixing ratio);

Other fungicidal compounds: tolclofos-methyl, thiram, captan, carbendazim, thiophanate-methyl, mancozeb, thiabendazole, isotianil, ethaboxam, picarbutrazox, oxathiapiprolin, and triazoxide;

Plant growth regulators: ethephon, chlormequat-chloride, mepiquat-chloride, and 4-oxo-4-(2-phenylethyl)aminobutyric acid.

[4] The control method according to [2] or [3], wherein one or more compounds selected from the compound group B is one or more compounds selected from the group consisting of the following compounds, Strobilurin compounds: pyraclostrobin, azoxystrobin, mandestrobin, trifloxystrobin, and picoxystrobin;

Azole compounds: prothioconazole, epoxyconazole, tebuconazole, cyproconazole, propiconazole, metconazole, bromuconazole, tetraconazole, triticonazole, ipfentrifluconazolle, and mefentrifluconazole;

SDHI compounds: benzobindiflupyr, bixafen, fluxapyroxad, N-(7-fluoro-1,1,3-trimethylindan-4-yl)-1-methyl-3-difluoromethylpyrazole-4-carboxamide (including a racemate or an enantiomer and a mixture of an B enantiomer and an S enantiomer at any mixing ratio), and N-(1,1,3-trimethylindan-4-yl)-1-methyl-3-difluoromethylpyrazole-4-carboxamide (including a racemate or an enantiomer and a mixture of an R enantiomer and an S enantiomer at any mixing ratio);

Other fungicidal compounds: tolclofos-methyl and ethaboxam;

Pyrethroid compounds: bifenthrin, lambda-cyhalothrin, gamma-cyhalothrin, cypermethrin, fenpropathrin, etofenprox, silafluofen, and esfenvalerate;

Benzoylphenylurea compound: teflubenzuron and triflumuron;

Organic phosphorus insecticidal compounds: acephate and methomyl;

Neonicotinoid compounds: imidacloprid, clothianidin, thiamethoxam, sulfoxaflor, flupyradifurone, triflumezopyrim, and dicloromezotiaz;

Diamide compounds: flubendiamide, chlorantraniliprole, cyantraniliprole, broflanilide, tetraniliprole, and cyhalodiamide.

[5] The control method according to [1] or [2], wherein the cultivation area of crops is treated with ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate before sowing the crop seeds.

[6] The control method according to [1] or [2], wherein the cultivation area of crops is treated with ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate simultaneously with sowing the crop seeds.

[7] The control method according to [1] or [2], wherein the cultivation area of crops is treated with ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate after sowing the crop seeds.

[8] The control method according to any one of [2] to [7], wherein the harmful organisms are weeds and/or arthropods and/or plant pathogens.

[9] The control method according to any one of [2] to [7], wherein the harmful organisms are weeds.

[10] The control method according to any one of [2] to [9], wherein the crops are selected from the group consisting of soybeans, corn, cotton, rapeseed, rice, wheat, barley, sugarcane, sugar beet, sorghum, and sunflower.

Effect of the Invention

Harmful organisms in a cultivation area of crops can be controlled by performing the method for controlling harmful organisms of the present invention.

MODE FOR CARRYING OUT THE INVENTION

The method for controlling weeds of the present invention comprises a step of treating a cultivation area of crops with ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (hereinafter, referred to as a compound X) before, simultaneously with, and/or after sowing crop seeds.

The method for controlling harmful organisms of the present invention (hereinafter, referred to as the present method for controlling harmful organisms) comprises the steps (1) treating crop seeds with one or more compounds selected from the compound group A (hereinafter, also referred to as a step (1)); (2) treating a cultivation area of crops with the compound X before, simultaneously with, and/or after sowing the crop seeds obtained by the above-described step (hereinafter, referred to as a step (2)); and (3) performing a foliage treatment on crops with one or more compounds selected from the compound group B during a growing period of the crops (hereinafter, referred to as a step (3)).

The compound X a known compound and is represented by Formula (I). The compound X can be produced using known methods such as a method described in U.S. Pat. No. 6,537,948.

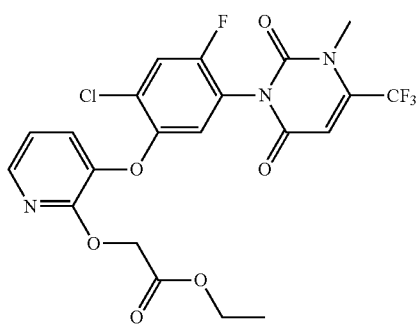

(I)

In the present invention, the crops are not limited as long as the crops are a type which can usually be cultivated as crops, and examples thereof include corn, cotton, rapeseed, rice, wheat, barley, sugarcane, sugar beet, sorghum, and sunflower.

Examples of such plants include plants to which tolerance to a PPO inhibitor such as flumioxazine; a 4-hydroxyphenylpyruvate dioxygenase inhibitor such as isoxaflutole; an acetolactate synthase (hereinafter, abbreviated as ALS) inhibitor such as imizethapyr and thifensulfuron-methyl; a 5-enolpyruvylshikimate 3-phosphate synthase (hereinafter, abbreviated as EPSP) inhibitor such as glyphosate; a glutamine synthase inhibitor such as glufosinate; an auxin type herbicide; an acetyl CoA carboxylase (hereinafter, abbreviated as ACCase) inhibitor such as sethoxydim; or a PSII inhibitor such as bromoxynil, is imparted by a traditional breeding method, genome editing, or a genetic engineering technique.

Examples of the plants to which tolerance is imparted by a traditional breeding method include STS soybeans having tolerance to a sulfonylurea ALS inhibiting herbicide such as thifensulfuron-methyl. Similarly, examples of the plants to which tolerance is imparted by a traditional breeding method include rice, wheat, corn, rapeseed, and sunflower having tolerance to an imidazolinone ALS inhibitor, and these are already commercially available under the product names of Clearfield (registered trademark) and Express (registered trademark). Similarly, examples of the plants to which tolerance is imparted by a traditional breeding method include corn and rice which are tolerant to an ACCase inhibitor, which have the product names of PoastProtected (registered trademark), Provisia (registered trademark) and the like. Similarly, examples of the plants to which tolerance is imparted by a traditional breeding method include Triazine Tolerant rapeseed having tolerance to a PSII inhibitor.

Further, examples of the plants to which tolerance is imparted by a genetic engineering technique include soybeans, corn, cotton, and rapeseed having tolerance to glyphosate, and these are already commercially available under the product names of RoundupReady (registered trademark) and Gly-Tol (registered trademark). Similarly, there are soybeans having tolerance to glufosinate by genetic engineering technique, and these are already commercially available under the product name of LibertyLink (registered trademark), etc. There are varieties of soybeans and corn which have tolerance to both of glyphosate and an ALS inhibitor, and these have the product names of Optimum GAT (registered trademark). Similarly, there are soybeans having tolerance to an imidazolinone ALS inhibitor by genetic engineering technique and these soybeans have been developed under the product name of Cultivance.

Crops having tolerance to an aryloxyphenoxy herbicide such as quizalofop, haloxyfop, fluazifop, diclofop, fenoxaprop, metamifop, cyhalofop, or clodinafop can be produced by transforming a gene encoding aryloxyalkanoate dioxygenase, and there are varieties of soybeans having the product name of Enlist (registered trademark).

Examples of the above-described plants include plants which are capable of synthesizing, for example, selective toxins that are known as genus *Bacillus* using a genetic engineering technique.

Examples of toxins expressed by such genetically modified plants include insecticidal proteins derived from *Bacillus cereus* or *Bacillus popilliae*; δ-endotoxin such as Cry1Ab, Cry1Ac, Cry1F, Cry1Fa2, Cry2Ab, Cry3A, Cry3Bb1, and Cry9C derived from *Bacillus thuringiensis*; insecticidal proteins such as VIP1, VIP2, VIP3, and VIP3A; insecticidal proteins derived from nematodes; toxins produced by animals such as scorpion toxins, spider toxins, bee toxins, and insect-specific neurotoxins; filamentous fungi toxins; plant lectin; agglutinin; a protease inhibitor such as a trypsin inhibitor, a serine protease inhibitor, patatin, cystatin, or a papain inhibitor; ribosome inactivating protein (RIP) such as ricin, corn-RIP, abrin, luffin, saporin, and briodin; a steroid metabolizing enzyme such as 3-hydroxysteroid oxidase, ecdysteroid-UDP-glycosyltransferase, and cholesterol oxidase; an ecdysone inhibitor; HMG-CoA reductase; an ion channel inhibitor such as a sodium channel and a calcium channel inhibitor; juvenile hormone esterase; a diuretic hormone receptor; stilbene synthase; bibenzyl synthase; chitinase; and glucanase.

Further, examples toxins expressed by such genetically modified crops also include δ-endotoxin proteins such as Cry1Ab, Cry1Ac, Cry1F, Cry1Fa2, Cry2Ab, Cry3A, Cry3Bb1, Cry9C, Cry34Ab, and Cry35Ab; hybrid toxins of insecticidal proteins such as VIP1, VIP2, VIP3, and VIP3A; partially defected toxins; and modified toxins. Hybrid toxins are produced by a new combination of different domains of these proteins using a recombination technology. As partially defected toxins, Cry1Ab in which a part of the amino acid sequence is deleted is known. One or a plurality of amino acids of naturally occurring toxins are substituted in the modified toxins. Examples of these toxins and the recombinant plants which are capable of synthesizing these toxins are described in EP-A-0374753, WO93/07278, WO95/34656, EP-A-0427529, EP-A-451878, WO03/052073, and the like. The toxins contained in these recombinant plants impart, to the plants, resistance to Coleopteran pests, Diptera pests, and Lepidoptera insect pests.

Further, recombinant plants which contain one or a plurality of insecticidal genes having resistance to insect pests and express one or a plurality of toxins have already been known and some of them are commercially available. Examples of these recombinant plants include Intacta (registered trademark). Examples of plants used in the present invention also include plants imparted with resistance to aphids such as Rag1 (Resistance Aphid Gene 1) gene-transformed soybeans.

Further, examples of the plants used in the present invention include plants to which resistance to nematodes is imparted using a traditional breeding method or a genetic engineering technique. As the genetic engineering technique used for imparting resistance to nematodes, RNAi is exemplified.

Examples of the above-described plants include plants to which ability for producing anti-pathogenic substances having a selective action is imparted using a genetic engineering technique. As examples of the anti-pathogenic substances, PR proteins and the like have been known (PRPs, EP-A-0392225). The anti-pathogenic substances and the recombinant plants producing the anti-pathogenic substances are described in EP-A-0392225, WO95/33818, and PP-A-0353191. Examples of the anti-pathogenic substances expressed in such recombinant plants include ion channel inhibitors such as a sodium channel inhibitor and a calcium channel inhibitor (toxins such as KP1, KP4, and KP6 produced by viruses are known); stilbene synthase; bibenzyl synthase; chitinase; glucanase; PR proteins; and anti-pathogenic substances produced by microorganisms such as peptide antibiotics, antibiotics having heterocycles, protein factors associated with plant disease resistance (referred to as plant disease resistance genes and described in WO03/000906).

Examples of the above-described plants include plants to which useful traits such as trait improving oil component or trait increasing content of amino acid are imparted using a genetic engineering technique. Examples thereof include VISTIVE (registered trademark), which is low linolenic soybeans obtained by reducing the linolen content. In addition, other examples thereof include plants to which tolerance to environmental stress is imparted using a genetic engineering technique. Examples of the crops include DroughtGard (registered trademark).

Further, other examples thereof include stack varieties obtained by combining a plurality of useful traits such as the above-described conventional herbicidal trait or herbicide tolerant genes, insecticidal pest resistant gene, anti-pathogenic substance producing genes, trait improving oil component and trait increasing content of amino acid. Other examples thereof include plants generated using a genome editing technology in place of a genetic engineering technique.

In the present method for controlling harmful organisms, the compound group A is the group consisting of a neonicotinoid compound, a diamide compound, a carbamate compound, an organic phosphorus compound, a biological nematicidal compound, other insecticidal compounds and nematicidal compounds, an azole compound, a strobilurin compound, a metalaxyl compound, an SDHI compound, and other fungicidal compounds and plant growth regulators.

In the present method for controlling harmful organisms, examples of the neonicotinoid compounds used to treat crop seeds include clothianidin, imidacloprid, nitenpyram, acetamiprid, thiamethoxam, flupyradifurone, sulfoxaflor, triflumezopyrim, dicloromezotiaz, thiacloprid, and dinotefuran.

In the present method for controlling harmful organisms, examples of the diamide compounds used to treat crop seeds include flubendiamide, chlorantraniliprole, cyantraniliprole, cyclaniliprole, broflanilide, tetraniliprole, and cyhalodiamide.

In the present method for controlling harmful organisms, examples of the carbamate compounds include aldicarb, oxamyl, thiodicarb, carbofuran, carbosulfan, and dimethoate.

In the present method for controlling harmful organisms, examples of the organic phosphorus compounds used to treat crop seeds include fenamiphos, imicyafos, fensulfothion, terbufos, fosthiazate, phosphocarb, dichlofenthion, isamidofos, isazophos, ethoprophos, cadusafos, chlorpyrifos, heterofos, mecarphon, phorate, thionazin, triazophos, diamidafos, fosthietan, and phosphamidon.

In the present method for controlling harmful organisms, examples of the biological nematicidal compounds used to treat crop seeds include Harpin Protein, *Pasteuria nishizawae*, *Pasteuria penetrans*, *Pasteuria usage*, *Myrothecium verrucaria*, *Burholderia cepacia*, *Bacillus chitonosporus*, *Paecilomyces lilacinus*, *Bacillus amyloliquefaciens*, *Bacillus firmus*, *Bacillus subtilis*, *Bacillus pumulus*, *Trichoderma harzianum*, *Hirsutella rhossiliensis*, *Hirsutella minnesotensis*, *Verticillium chlamydosporum*, and *Arthrobotrys dactyloides*.

In the present method for controlling harmful organisms, examples of other insecticidal compounds and nematicidal compounds used to treat crop seeds include fipronil, ethiprole, beta-cyfluthrin, tefluthrin, chlorpyrifos, abamectin, spirotetramat, tioxazafen, fluazaindolizine, fluensulfone, and fluxametamide.

In the present method for controlling harmful organisms, examples of the azole compounds used to treat crop seeds include azaconazole, bitertanol, bromuconazole, cyproconazole, difenoconazole, diniconazole, epoxyconazole, fenbuconazole, fluquinconazole, flusilazole, flutriafol, hexaconazole, imibenconazole, ipconazole, metconazole, myclobutanil, penconazole, propiconazole, prothioconazole, simeconazole, tebuconazole, tetraconazole, triadimenol, triticonazole, fenarimol, nuarimol, pyrifenox, imazalil, oxpoconazole fumarate, pefurazoate, prochloraz, triflumizole, ipfentrifluconazole, and mefentrifluconazole.

In the present method for controlling harmful organisms, examples of the strobilurin compound used to treat crop seeds include kresoxim-methyl, azoxystrobin, trifloxystrobin, fluoxastrobin, picoxystrobin, pyraclostrobin, dimoxystrobin, pyribencarb, metominostrobin, orysastrobin, and mandestrobin.

In the present method for controlling harmful organisms, examples of the metalaxyl compound used to treat crop seeds include metalaxyl and metalaxyl-M (mefenoxam).

In the present method for controlling harmful organisms, examples of the SDHI compound used to treat crop seeds include sedaxane, penflufen, carboxin, boscalid, furametpyr, flutolanil, fluxapyroxad, isopyrazam, fluopyram, isofetamid, pyraziflumid, pydiflumetofen, N-(7-fluoro-1,1,3-trimethyl-indan-4-yl)-1-methyl-3-difluoromethylpyrazole-4-carboxamide (including a racemate or an enantiomer and a mixture of an R enantiomer and an S enantiomer at any mixing ratio, and a compound, rich in R enantiomer, in which the ratio of the R enantiomer to the S enantiomer is 80:20 or greater is also referred to as F9990 below), N-(1,1,3-trimethylindan-4-yl)-1-methyl-3-difluoromethylpyrazole-4-carboxamide (including a racemate or an enantiomer and a mixture of an R enantiomer and an S enantiomer at any mixing ratio, and a compound, rich in R enantiomer, in which the ratio of the R enantiomer to the S enantiomer is 80:20 or greater is also referred to as a compound 1 below), and thifluzamide.

In the present method for controlling harmful organisms, examples of the plant growth regulators used to treat crop seeds include ethephon, chlormequat-chloride, mepiquat-chloride, and 4-oxo-4-(2-phenylethyl)aminobutyric acid (hereinafter, also referred to as a compound 2).

In the present method for controlling harmful organisms, examples of other fungicidal compounds used to treat crop seeds include tolclofos-methyl, thiram, captan, carbendazim, thiophanate-methyl, mancozeb, thiabendazole, isotianil, triazoxide, picarbutrazox, and oxathiapiprolin.

The compounds constituting the above-described compound group A are all known compounds and can be synthesized based on known technical literatures. Further, commercially available formulations or standard products can be purchased and then used.

In the present method for controlling harmful organisms, the compound group B is the group consisting of a strobilurin compound, an azole compound, an SDHI compound, other fungicidal compounds, a pyrethroid compound, a benzoylphenylurea compound, an organic phosphorus insecticide compound, a neonicotinoid compound, and a diamide compound.

In the present method for controlling harmful organisms, examples of the strobilurin compound used to perform a foliage treatment on crops include pyraclostrobin, azoxystrobin, mandestrobin, trifloxystrobin, and picoxystrobin.

In the present method for controlling harmful organisms, examples of the azole compounds used to perform a foliage treatment on crops include prothioconazole, epoxyconazole, tebuconazole, cyproconazole, propiconazole, metconazole, bromuconazole, tetraconazole, triticonazole, ipfentrifluconazole, and mefentrifluconazole.

In the present method for controlling harmful organisms, examples of the SDHI compounds used to perform foliage treatment on crops include benzobindiflupyr, bixafen, fluxapyroxad, F9990, and the compound 1.

In the present method for controlling harmful organisms, examples of other fungicidal compounds used to perform a foliage treatment on crops include tolclofos-methyl and ethaboxam.

In the present method for controlling harmful organisms, examples of the pyrethroid compounds used to perform a foliage treatment on crops include bifenthrin, lambda-cyhalothrin, gamma-cyhalothrin, cypermethrin, fenpropathrin, etofenprox, silafluofen, and esfenvalerate.

In the present method for controlling harmful organisms, examples of the benzoylphenylurea compounds used to perform a foliage treatment on crops include teflubenzuron and triflumuron.

In the present method for controlling harmful organisms, examples of the organic phosphorus insecticidal compounds used to perform a foliage treatment on crops include acephate and methomyl.

In the present method for controlling harmful organisms, examples of the neonicotinoid compounds used to perform a foliage treatment on crops include imidacloprid, clothianidin, thiamethoxam, sulfoxaflor, flupyradifurone, triflumezopyrim, and dicloromezotiaz.

In the present method for controlling harmful organisms, examples of the diamide compounds used to perform a foliage treatment on crops include flubendiamide, chlorantraniliprole, cyantraniliprole, broflanilide, tetraniliprole, and cyhalodiamide.

The compounds constituting the above-described compound group B are all known compounds and can be synthesized based on known technical literatures. Further, commercially available formulations or standard products can be purchased and then used.

In the step of treating the crop seeds with one or more compounds (hereinafter, referred to as compounds A) selected from the compound group A according to the present method for controlling harmful organisms, the compounds A are usually mixed with carriers such as solid carriers or liquid carriers, an auxiliary agents for formulation such as a surfactant is added thereto as necessary, and the mixture is formulated and then used. A preferable formulation type is an aqueous liquid suspension formulation.

For the compounds A, a formulation consisting of single ingredient may be used solely, two or more formulations consisting of single ingredient may be used in combination, or a formulation consisting of two or more ingredients may be used.

The application rate of the compounds A is usually in a range of 0.2 to 5,000 g and preferably in a range of 0.5 to 1,000 g per 100 kg of crop seeds. Examples of the method for treating the crop seeds with the compounds A include a method for powder-coating crop seeds with a formulation that contains the compounds A, a method for immersing crop seeds in a formulation that contains the compounds A, a method for spraying a formulation that contains the compounds A to crop seeds, and a method for coating crop seeds with a mixture of the compounds A and carriers.

In the method for controlling weeds of the present invention and the present method for controlling harmful organisms, a cultivation area of crop seeds is treated with a compound X before, simultaneously with, and/or after sowing the crop seeds.

The cultivation area of crops in the present invention is not particularly limited as long as the cultivation area is a place where crops are cultivated, and examples thereof include a farmland, a field, a non-agricultural area, a park, a bank, a seedling tray, a seedling box, and a nursery field.

In the step of treating the cultivation area of crops with the compound X, the compound X is usually mixed with carriers such as solid carriers or liquid carriers, an auxiliary agents for formulation such as a surfactant is added thereto as necessary, and the mixture is formulated and then used. Preferable formulation types are an aqueous liquid suspension formulation, a wettable powder, a water dispersible granule, a granular formulation, and an emulsifiable concentrate, and a more preferable formulation type is an emulsifiable concentrate. During the step, a formulation containing the compound X as a single ingredient may be used alone or may be used mixing with formulations containing other herbicides as active ingredients. Alternatively, a formulation containing the compound X and other herbicides as active ingredients may be used by itself, or may be used mixing with formulations containing yet another herbicides as active ingredients.

Examples of the method for treating a cultivation area of crops with the compound X include a method for spraying the compound X to the soil of the cultivation area of crops and a method for spraying the compound X to weeds after the weeds are emerged.

The application rate of the compound X is usually in a range of 1 to 1,000 g, preferably in a range of 2 to 500 g, more preferably in a range of 5 to 200 g, and still more preferably in a range of 10 to 100 g per 10,000 $m^2$ of a cultivation area of crops. Further, in the step of treating the cultivation area of crops with the compound X, the cultivation area may be treated with the compound X mixing an adjuvant. The type of adjuvant is not particularly limited, and examples thereof include oils such as Agri-Dex and MSO; nonions (ester or ether of polyoxyethylene) such as Induce; anions (substituted sulfonate) such as Dramin S, cations (polyoxyethylene amine) such as Genamin T 200 BM; and organic silicon-based adjuvants such as Silwett L77.

The pH or the hardness of the spray liquid at the time of treating the cultivation area of crops with the compound X is not particularly limited, but the pH thereof is usually in a range of 5 to 9 and the hardness thereof is usually in a range of 0 to 500.

The period of time for treating the cultivation area of crops with the compound X is not particularly limited, but is usually between 5 am and 9 pm and the photon flux density is usually in a range of 10 to 2,500 $\mu mol/m^2/sec$.

In the method for controlling weeds of the present invention and the present method for controlling harmful organisms, crop seeds are sowed in a cultivation area using a typical method. The cultivation area of crops may be treated with the compound X before, simultaneously with, and/or after sowing the crop seeds. In other words, the compound X is applied once before, simultaneously with, or after sowing the crop seeds; twice except before the sowing, twice except simultaneously with the sowing, or twice except after the sowing; or three times before, simultaneously with, and after the sowing.

In a case where the cultivation area is treated with the compound X before sowing the crop seeds, the cultivation area is treated with the compound X usually during a period of 50 days before the sowing to immediately before the sowing, preferably during a period of 30 days before the sowing to immediately before the sowing, more preferably during a period of 20 days before the sowing to immediately before the sowing, and still more preferably during a period of 10 days before the sowing to immediately before the sowing.

In a case where the cultivation area is treated with the compound X after sowing crop seeds, the cultivation area is treated with the compound X usually during a period of immediately after the sowing to before blooming and more preferably during a period of immediately after the sowing to before sprouting and a period of the 1 to 6 leaf stage of crops. In a case where the cultivation area is subjected to a foliage treatment with the compound X during a period of the 1 to 6 leaf stage of crops, the step (3) may be performed concurrently by mixing the compound X with one or more compounds (hereinafter, referred to as compounds B) selected from the above-described compound group B or may be performed sequentially. In a case where the steps are performed sequentially, the order thereof is not particularly limited.

The case where the cultivation area is treated with the compound X simultaneously with sowing the crop seeds is a case where a sowing machine and a spraying machine are integrated with each other.

In the step (3) of the present method for controlling harmful organisms, the compounds B are usually mixed with carriers such as solid carriers or liquid carriers, an auxiliary agents for formulation such as a surfactant is added thereto as necessary, and the mixture is formulated and then used. Preferred examples of the formulation types include an emulsifiable concentrate, an aqueous suspension, and a soluble liquid.

The period of when the step (3) is performed is preferably a period of 10 days to 120 days after the sowing and more preferably a period of 21 days to 90 days after the sowing. In a case of a plurality of compounds B, a plurality of formulations containing each of compounds B as an active ingredient may be used. During this time, the formulations may be treated mixing with each other or may be sequentially treated. Further, a mixed formulation containing a plurality of compounds as active ingredients may be used.

The application rate of the compounds B is usually in a range of 5 to 5,000 g, preferably in a range of 20 to 2,000 g, and more preferably in a range of 50 to 1,500 g per 10,000 m$^2$ of the cultivation area of crop seeds. Further, during the step (3), the compounds B are mixed with an adjuvant and then used for the treatment.

According to the method for controlling weeds of the present invention, weeds can be controlled. According to the present method for controlling harmful organisms, harmful organisms such as harmful arthropods, harmful nematodes, and/or plant pathogens, and weeds can be controlled.

Examples of the harmful arthropods include the followings:

Hemipteran pests, for example,
Delphacidae (Planthoppers) such as *Laodelphax striatellus, Nilaparvata lugens, Sogatella furcifera*;
Deltocephalidae (Leafhoppers) such as *Nephotettix cincticeps* and *Nephotettix virescens*;
Aphididae (Aphids) such as *Aphis gossypil, Myzus persicae, Brevicoryne brassicae, Macrosiphum euphorbiae, Aulacorthum solani, Rhopalogiphum padi*, and *Toxoptera citricidus*;
Pentatomidae (Stink bugs) such as *Nezara antennata, Riptortus clavetus, Leptocorisa chinensis, Eysarcoris parvus, Halyomorpha mista*, and *Lygus lineolaris*;
Aleyrodidae (Whiteflies) such as *Trialeurodes vaporariorum, Bemisia tabaci*, and *Bemisia argentifolii*;
Coccoide (Scale insects) such as *Aonidiella aurantii, Comstockaspis perniciosa, Unaspis citri, Ceroplastes rubens*, and *Icerya purchasi*;
Tingidae (Lace bugs); and
Psyllidae (Jumping plant lice);
Lepidoptera insect pests, for example,
Pyralidae such as *Chilo suopressalis, Tryporyza incertulas, Cnaphalocrocis medinalis, Notarcha derogata, Plodia interpunctella, Ostrinia furnacalis, Ostrinia nubilaris, Hellula undalis*, and *Pediasia teterrellus*;
Noctuidae such as *Spodoptera litura, Spodoptera exigua, Pseudaletia separata, Mamestra brassicae, Agrotis ipsilon, Plusia nigrisigna, Trichopiusia* spp., *Heliothis* spp., and *Helicoverpa* spp.; and
Pieridae such as *Pieris rapae*;
Tortricidae (Budworms) such as *Grapholita molesta, Leguminivora glycinivorella, Matsumuraeses azukivora, Adoxophyes orana fasciata, Adoxophyes* sp., *Homona magnanima, Archips fuscocupreanus*, and *Cydia pomonella*;
Gracillariidae such as *Caloptilia theivora* and *Phyllonorycter ringoneella*;
Carpocapsa pomonellas such as *Carposina niponensis*;
Lyonetiidae (Leafminer moths) such as *Lyonetia* spp.;
Lymantriidae (Tussock moths) such as *Lymantriidae* spp., and *Euproctis* spp.;
Yponomeutidae such as *Plutella xylostella*;
Gelechiidae such as *Pectinophora gossypiella* and *Phthorimaea operculella*;
Arctiidae (Tiger moths) such as *Hyphantria cunea*; and
Tineidae (Tineids) such as *Tinea translucens* and *Tineola bissellielia*;
Thysanoptera pests, for example,
Thysanoptera (Thrips) such as *Frankliniella occidentalis, Thrips parmi, Scirtothrips dorsalis, Thrips tabaci, Frankliniella intonsa*, and *Frankliniella fusca*;
Diptera pests, for example,
Agromyzidae such as *Musca domestica, Culex pipiens pallens, Tabanus trigonus, Hylemya antiqua, Hylemya platura, Anopheles sinensis, Agromyza oryzae, Hydrellia griseola, Chlorops oryzae*, and *Liriomyza trifolii*;
*Dacus cucurbitae*;
*Ceratitis capitata*;
Coleopteran pests, for example,
*Epilachna vigintioctopunctata, Aulacophora femoralis, Phyllotreta striolata, Oulema oryzae, Echinocnemus squameus, Lissorhoptrus oryzophilus, Anthonomus grandis, Callosobruchus chinensis, Sphenophorus venatus, Popillia japonica, Anomala cuprea, Diabrotica* spp., *Leptinotarsa decemlineata, Agriotes* spp., *Lasioderma serri-*

*corne, Anthrenus verbasci, Tribolium castaneum, Lyctus brunneus, Anoplophora malasiaca,* and *Tomicus piniperda;*

Orthoptera pests, for example,

*Locusta migratoria, Gryllotalpa africana, Oxya yezoensis,* and *Oxya japonica;*

Hymenoptera pests, for example,

*Psthalia rosae, Acromyrmex* spp., and *Solenopsis* spp.;

Blattaria pests, for example, *Blattella germanica, Periplaneta fuliginosa, Periplaneta americana, Periplaneta brunnea,* and *Blatta orientalis;*

Acarina pests, for example,

Tetranychidae such as *Tetranychus urticae, Panonychus citri, Oligonychus* spp.;

Eriophyidae (Gall mites) such as *Aculops pelekassi;*

Tarsonemidae (White mites) such as *Polyphagotarsonemus latus;*

Tenuipalpidae;

Tuckerellidae;

Acaridae such as *Tyrophagus putrescentiae;*

Pyroglyphidae such as *Dermatophagoides farinae* and *Dermatophagoides ptrenyssnus;* and Cheyletidae such as *Cheyletus eruditus, Cheyletus malaccensis,* and *Cheyletus moorei.*

Examples of the plant pathogens include the followings:
*Cercospora gossypina, Cercospora kikuchii, Cercospora zeae-maydis, Cercospora sojina, Phakopsora gossypii, Rhizoctonia solani, Colletotrichum gossypii, Peronospora gossypina, Aspergillus* spp., *Penicillium* spp., *Fusarium* spp., *Tricoderma* spp., *Thielaviopsis* spp., *Rhizopus* spp., *Mucor* spp., *Corticium* spp., *Phoma* spp., *Diplodia* spp., *Verticillium* spp., *Puccinia* spp., *Mycosphaerella* spp., *Phytophtora* spp. (*Phytophthora sojae, Phytophthora nicotianae* var. nicotianae, *Phytophthora infestans, Phytophthora erythroseptica,* etc.), *Pythium* spp. (*Pythium debaryanum, Pythium sylvaticum, Pythium graminicola, Pythium irregulare, Pythium ultimum,* etc.), *Microsphaera diffusa, Diaporthe phaseolorum* var. *sojae, Septoria glycines, Phakopsora pachyrhizi, Sclerotinia sclerotiorum, Elsinoe glycines, Ustilago maydis, Cochliobolus heterostrophus, Gloeocercospora sorghi,* and *Alternaria* spp.

Examples of the weeds include the followings.

Urticaceae weeds: himeirakusa (small nettle; *Urtica ureas*)

Polygonaceae weeds: sobakazura (black bindweed; *Polygonum convolvulus*), sanaetade (pale persicaria; *Polygonum lapathifolium*), amerikasanaetade (Pennsylvania smartweed; *Polygonum pensylvanicum*), harutade (redshank; *Polygonum persicaria*), inutade (bristly lady's-thumb; *Polygonum longisetum*), michiyanagi (knotgrass; *Polygonum aviculare*), haimichiyanagi (equal-leaved knotgrass; *Polygonum arenastrum*), itadori (Japanese knotweed; *Polygonum cuspidatum*), gishigishi (Japanese dock; *Rumex japonicus*), nagabagishigishi (curly dock; *Rumex crispus*), ezonogishigishi (blunt-leaved dock; *Rumex obtusifolius*), suiba (common sorrel; *Rumex acetosa*)

Portulacaceae weeds: suberihiyu (common purslane; *Portulaca oleracea*)

Caryophyllaceae weeds: hakobe (common chickweed; *Stellaria media*), miminagusa (common mouse-ear; *Cerastium holosteoides*), orandamiminagusa (sticky mouse-ear; *Cerastium glomeratum*), otsumekusa (corn spurrey; *Spergula arvensis*), mantema (five-wound catchfly; *Silene gallica*)

Molluginaceae weeds: kurumabazakuroso (carpetweed; *Mollugo verticillata*)

Chenopodiaceae weeds: shiroza (common lambsquarters; *Chenopodium album*), kearitaso (Indian goosefoot; *Chenopodium ambrosioides*), hokigi (kochia; *Kochia scoparia*), noharahijiki (spiny saltwort; *Salsola kali*), Orach (*Atriplex* spp.)

Amaranthaceae weeds: aogeito (redroot pigweed; *Amaranthus retroflexus*), aobiyu (slender amaranth; *Amaranthus viridis*), inubiyu (livid amaranth; *Amaranthus lividus*), haribiyu (spiny amaranth; *Amaranthus spinosus*), honagaaogeito (smooth pigweed; *Amaranthus hybridus*), ohonagaaogeito (Palmer amaranth; *Amaranthus palmeri*), hosobainubiyu (common waterhemp; *Amaranthus rudis*), hosoaogeito (green pigweed; *Amaranthus patulus*), hiyumodoki (tall waterhemp; *Amaranthus tuberculatus*), amerikabiyu (prostrate pigweed; *Amaranthus blitoides*), haibiyu (large-fruit amaranth; *Amaranthus deflexus*), mucronate amaranth (*Amaranthus quitensis*), nagaetsurunogeito (alligator weed; *Alternanthera philoxeroides*), tsurugeito (sessile alligator weed; *Alternanthera sessilis*), sanguinaria (perrotleaf; *Alternanthera tenella*)

Papaveraceae weeds: hinageshi (common poppy; *Papaver rhoeas*), azamigeshi (Mexican prickle poppy; *Argemone mexicana*)

Brassicaceae weeds: seiyonodaikon (wild radish; *Raphanus raphanistrum*), Radish (*Raphanus sativus*), noharagarashi (wild mustard; *Sinapis arvensis*), nazuna (shepherd's purse; *Capsella bursa-pastoris*), seiyokarashina (white mustard; *Brassica juncea*), seiyoaburana (field mustard, *Brassica campestris*), himekujiragusa (pinnate tansy mustard; *Descurainia pinnata*), sukashitagobo (marsh yellowcress; *Rorippa islandica*), kirehainugarashi (yellow fieldcress; *Rorippa sylvestris*), gumbainazuna (field pennycress; *Thlaspi arvense*), miyagarashi (turnip weed; *Myagrum rugosum*), mamegumbainazuna (Virginia pepperweed; *Lepidium virginicum*), karakusanazuna (slender wartcress; *Coronopus didymus*)

Capparaceae weeds: African cabbage (*Cleome affinis*)

Fabaceae weeds: kusanemu (Indian joint vetch; *Aeschynomene indica*), zigzag joint vetch (*Aeschynomene rudis*), amerikatsunokusanemu (hemp sesbania; *Sesbania exaltata*), ebisugusa (sickle pod; *Cassia obtusifolia*), habuso (coffee senna; *Cassia occidentalis*), juzuhagi (Florida beggar weed; *Desmodium tortuosum*), noharahagi (wild groundnut; *Desmodium adscendens*), shirotsumekusa (white clover; *Trifolium repens*), kuzu (kudzu; *Pueraria lobata*), karasunoendo (narrowleaf vetch; *Vicia angustifolia*), tanukikomatsunagi (hairy indigo; *Indigofera hirsuta*), *Indigofera truxillensis,* yaseisasage (common cowpea; *Vigna sinensis*)

Oxalidaceae: katabami (creeping wood sorrel; *Oxalis corniculata*), ottachikatabami (European wood sorrel; *Oxalis strica*), purple shamrock (*Oxalis oxyptera*)

Geraniaceae weeds: amerikafuro (Carolina geranium; *Geranium carolinense*), orandafuro (common storksbill; *Erodium cicutarium*)

Euphorbiaceae weeds: todaigusa (sun spurge; *Euphorbia helioscopia*), onishikiso (annual spurge; *Euphorbia maculata*), konishikiso (prostrate spurge; *Euphorbia humistrata*), hagikuso (Hungarian spurge; *Euphorbia esula*), shojoso (wild poinsettia; *Euphorbia heterophylla*), hyssop-leaf sandmat (*Euphorbia brasiliensis*), enokigusa (asian copperleaf; *Acalypha australis*), tropic croton (*Croton glandulosus*), lobed croton (*Croton lobatus*), burajirukomikanso (long-stalked phyllanthus; *Phyllanthus corcovadensis*), togoma (castor bean; *Ricinus communis*)

Malvaceae weeds: ichibi (velvetleaf; *Abutilon theophrasti*), kingojika (arrow-leaf *Sida; Sida rhombiforia*), marubakingojika (heart-leaf *Sida*; *Sida cordifolia*), amerikakingojika (prickly *Sida*; *Sida spinosa*), *Sida glaziovii*, *Sida santaremnensis*, ginsenka (bladder weed; *Hibiscus trionum*), nishikiaoi (spurred *Anoda*; *Anoda cristata*), enokiaoi (spine-seeded false-mallow; *Malvastrum coromandelianum*)

Sterculiaceae weeds: kobambanoki (Florida *Waltheria*; *Waltheria indica*)

Violaceae weeds: makibasumire (field violet; *Viola arvensis*), wairudopanji (wild violet; *Viola tricolor*)

Cucurbitaceae weeds: arechiuri (bur cucumber; *Sicyos angulatus*), wild cucumber (*Echinocystis lobata*), yaseinigauri (bitter balsam apple; *Momordica charantia*)

Lythraceae weeds: ezomisohagi (purple loosestrife; *Lythrum salicaria*)

Apiaceae weeds: chidomegusa (lawn pennywort; *Hydrocotyle sibthorpioides*)

Sapindaceae weeds: fusenkazura (heartseed; *Cardiospermum halicacabum*)

Primulaceae weeds: akabanarurihakobe (scarlet pimpernel; *Anagellis arvensis*)

Asclepiadaceae weeds: otowata (common milkweed; *Asclepias syriaca*), honeyvine milkweed (*Ampelamus albidus*)

Rubiaceae weeds: catchweed bedstraw (*Galium aparine*), yaemugura (*Galium spurium* var. *echinospermon*) hirohafutabamugura (broadleaf buttonweed; *Spermacoce latifolia*), burajiruhashikagusamodoki (Brazil calla lily; *Richardia brasiliensis*), uingudofuarusubotanuido (broadleaf buttonweed; *Borreria alata*)

Convolvulaceae weeds: asagao (Japanese morning glory; *Ipomoea nil*), amerikaasagao (ivy-leaf morning glory; *Ipomoea hederacea*), marubaasagao (tall morning glory; *Ipomoea purpurea*), marubaamerikaasagao (entire-leaf morning glory; *Ipomoea hederacea* var. *integriuscula*), mameasagao (pitted morning glory; *Ipomoea lacunosa*), hoshiasagao (three-lobe morning glory; *Ipomoea triloba*), noasagao (blue morning glory; *Ipomoea acuminata*), tsutanoharuko (scarlet morning glory; *Ipomoea hederifolia*), marubaruko (red morning glory; *Ipomoea coccinea*), rukoso (cypress-vine morning glory; *Ipomoea quamoclit*), *Ipomoea grandifolia*, *Ipomoea aristolochiafolia*, momijibahirugao (Cairo morning glory; *Ipomoea cairica*), seiyohirugao (field bindweed; *Convolvulus arvensis*), kohirugao (Japanese false bindweed; *Calystegia hederacea*), hirugao (Japanese bindweed; *Calystegia japonica*), tsutanohahirugao (ivy woodrose; *Merremia hedeacea*), hairy woodrose (*Merremia aegyptia*), roadside woodrose (*Merremia cissoides*), okinaasagao (small-flower morning glory; *Jacquemontia tamnifolia*)

Boraginaceae weeds: wasurenagusa (field forget-me-not; *Myosotis arvensis*)

Lamiaceae weeds: himeodorikoso (purple deadnettle; *Lamium purpureum*), hotokenoza (common henbit; *Lamium amplexicaule*), tamazakimehajiki (lion's ear; *Leonotis nepetaefolia*), nioinigakusa (wild spikenard; *Hyptis suaveolens*), *Hyptis lophanta*, mehaliki (Siberian motherwort; *Leonurus sibiricus*), yabuchorogi (field-nettle betony; *Stachys arvensis*)

Solanaceae weeds: yoshuchosenasagao (jimsonweed; *Datura stramonium*), inuhozuki (black nightshade; *Solanum nigrum*), teriminoinuhozuki (American black nightshade; *Solanum americanum*), amerakainuhozuki (eastern black nightshade; *Solanum ptycanthum*), keinuhozuki (hairy nightshade; *Solanum sarrachoides*), tomatodamashi (buffalo bur; *Solanum rostratum*), kinginnasubi (soda-apple nightshade; *Solanum aculeatissimum*), wairudotomato (sticky nightshade; *Solanum sisymbriifolium*), warunasubi (horse nettle; *Solanum carolinense*), sennarihozuki (cutleaf groundcherry; *Physalis angulata*), smooth groundcherry (*Physalis subglabrata*), osennari (apple of Peru; *Nicandra physaloides*)

Scrophulariaceae weeds: furasabaso (ivyleaf speedwell; *Veronica hederaefolia*), oinunofuguri (common speedwell; *Veronica persica*), tachiinunofuguri (corn speedwell; *Veronica arvensis*)

Plantaginaceae: obako (Asiatic plantain; *Plantago asiatica*)

Asteraceae weeds: onamomi (common cocklebur; *Xanthium pensylvanicum*), oonamomi (large cocklebur; *Xanthium occidentale*), yaseihimawari (common sunflower; *Helianthus annuus*), kamitsure (wild chamomile; *Matricaria chamomilla*), inukamitsure (scentless chamomile; *Matricaria perforata*), corn marigold (*Chrysanthemum segetum*), oroshagiku (rayless mayweed; *Matricaria matricarioides*), yomogi (Japanese mugwort; *Artemisia princeps*), oshuyomogi (common mugwort; *Artemisia vulgaris*), Chinese mugwort (*Artemisia verlotorum*), seitakaawadachiso (tall goldenrod; *Solidago altissima*), seiyotampopo (common dandelion; *Taraxacum officinale*), hakidamegiku (hairy galinsoga; *Galinsoga ciliata*), kogomegiku (smallflower galinsoga; *Galinsoga parviflora*), noborogiku (common groundsel; *Senecio vulgaris*), flower-of-souls (*Senecio brasiliensis*), *Senecio grisebachii*, arechinogiku (fleabane; *Conyza bonariensis*), himemukashiyomogi (marestail; *Conyza canadensis*), butakusa (common ragweed; *Ambrosia artemisiaefolia*), kuwamodoki (giant ragweed; *Ambrosia trifida*), kosendangusa (hairy beggarticks; *Bidens pilosa*), amerikasendangusa (common beggarticks; *Bidens frondosa*), greater beggarticks (*Bidens subalternans*), seiyotogeazami (Canada thistle; *Cirsium arvense*), amerikaoniazami (black thistle; *Cirsium vulgare*), mariaazami (blessed milkthistle; *Silybum marianum*), musk thistle (*Carduus nutans*), togechisha (prickly lettuce; *Lactuca serriola*), nogeshi (annual sowthistle; *Sonchus oleraceus*), oninogeshi (spiny sowthistle; *Sonchus asper*), beach creeping oxeye (*Wedelia glauca*), perfoliate blackfoot (*Melampodium perfoliatum*), usubeninigana (red tasselflower; *Emilia sonchifolia*), shiozakiso (wild marigold; *Tagetes minuta*), para cress (*Blainvillea latifolia*), kotobukigiku (coat buttons; *Tridax procumbens*), ieruba porosa (Bolivian coriander; *Porophyllum ruderale*), Paraguay starbur (*Acanthospermum australe*), bristly starbur (*Acanthospermum hispidum*), fusengazura (balloon vine; *Cardiospermum halicacabum*), kakkoazami (tropic *Ageratum*; *Ageratum conyzoides*), common boneset (*Eupatorium perfoliatum*), amerikatakasaburo (American false daisy; *Eclipta alba*), dandoborogiku (fireweed; *Erechtites hieracifolia*), amerikanebarasuteingu (American cudweed; *Gamochaeta spicata*), urajirochichikogusa (linear-leaf cudweed; *Gnaphalium spicatum*), Jageria hitora (*Jaegeria hirta*), gomagiku (ragweed *Parthenium*; *Parthenium hysterophorus*), menamomi (small yellow crownbeard; *Siegesbeckia orientalis*), merikentokinso (lawn burweed; *Soliva sessilis*)

Liliaceae weeds: wild onion (*Allium canadense*), wild garlic (*Allium vineale*)

Commelinaceae weeds: tsuyukusa (common dayflower; *Commelina communis*), marubatsuyukusa (tropical spiderwort; *Commelina bengharensis*), erect dayflower (*Commelina erecta*)

Poaceae weeds: inubie (common barnyardgrass; *Echinochloa crus-galli*), enokorogusa (green foxtail; *Setaria viridis*), akinoenokorogusa (giant foxtail; *Setaria faberi*), kinenokoro (yellow foxtail; *Setaria glauca*), amerikaenokorogusa (knotroot foxtail; *Setaria geniculata*), mehishiba (southern crabgrass; *Digitaria ciliaris*), large crabgrass (*Digitaria sanguinalis*), Jamaican crabgrass (*Digitaria horizontalis*), susukimehishiba (sourgrass; *Digitaria insularis*), ohishiba (goosegrass; *Eleusine indica*), suzumenokatabira (annual bluegrass; *Poa annua*), suzumenoteppo (short-awn foxtail; *Alospecurus aequalis*), blackgrass (*Alopecurus myosuroides*), karasumugi (wild oat; *Avena fatua*), seibammorokoshi (Johnsongrass; *Sorghum halepense*), shataken (grain *Sorghum*; *Sorghum vulgare*), shibamugi (quackgrass; *Agropyron repens*), nezumimugi (Italian ryegrass; *Lolium multiflorum*), hosomugi (perennial ryegrass; *Lolium perenne*), bomugi (rigid ryegrass; *Lolium rigidum*), karasunochahiki (cheat; *Bromus secalinus*), umanochahiki (downy brome; *Bromus tectorum*), hosonogemugi (foxtail barley; *Hordeum jubatum*), yagimugi (jointed goatgrass; *Aegilops cylindrica*), kusayoshi (reed canarygrass; *Phalaris arundinacea*), himekanarikusayoshi (little-seed canary grass; *Phalaris minor*), silky bentgrass (*Apera spica-venti*), okusakibi (fall *Panicum*; *Panicum dichotomiflorum*), Texas Panicum (*Panicum texanum*), gineakibi (guineagrass; *Panicum maximum*), merikennikukibi (broadleaf signalgrass; *Brachiaria platyphylla*), rujigurasu (Congo signal grass; *Brachiaria ruziziensis*), Alexander grass (*Brachiaria plantaginea*), Surinam grass (*Brachiaria decumbens*), palisade grass (*Brachiaria brizantha*), koronibiagurasu (creeping signalgrass; *Brachiaria humidicola*), shinkurinoiga (southern sandbur; *Cenchrus echinacus*), himekurinoiga (field sandbur; *Cenchrus pauciflorus*), narukobie (woolly cupgrass; *Eriochloa villosa*), penisetamu (feathery *Pennisetum*; *Pennisetum setosum*), afurikahigeshiba (Rhodes grass; *Chloris gayana*), oniwahokori (India lovegrass; *Eragrostis pilosa*), rubigaya (Natal grass; *Rhynchelitrum repens*), tatsunotsumegaya (crowfoot grass; *Dactyloctenium aegyptium*), taiwanaiashi (winkle grass; *Ischaemum rugosum*), yaseiine (common rice; *Oryza sativa*), amerikasuzumenohie (bahiagrass; *Paspalum notatum*), coastal sand *Paspalum* (*Paspalum maritimum*), kikuyugrass (*Pennisetum clandestinum*), hosobachikarashiba (West Indies *Pennisetum*; *Pennisetum setosum*), tsunoaiashi (itch grass; *Rottboellia cochinchinensis*)

Cyperaceae weeds: kayatsurigusa (Asian flatsedge; *Cyperus microiria*), kogomegayatsuri (rice flatsedge; *Cyperus iria*), kingayatsuri (fragrant flatsedge; *Cyperus odoratus*), hamasuge (purple nutsedge; *Cyperus rotundus*), kihamasuge (yellow nutsedge; *Cyperus esculentus*), himekugu (pasture spike sedge; *Kyllinga gracillima*)

Equisetaceae weeds: sugina (field horsetail; *Equisetum arvense*), inusugina (marsh horsetail; *Equisetum palustre*), etc.

Examples of the harmful nematodes include *Meloidogyne incognita*, *Meloidogyne javanica*, *Meloidogyne hapla*, *Meloidogyne arenari*, *Meloidogyne acronea*, *Ditylenchus destructor*, *Ditylenchus dipsaci*, *Pratylenchus penetrans*, *Pratylenchus cffeae*, *Pratylenchus loosi*, *Pratylenchus vulnus*, *Globodera rostochiensis*, *Globodera pallida*, *Heterodera glycines*, *Heterodera shachtoii*, *Aphelenchoides besseyi*, *Aphelenchoides ritzemabosi*, *Aphelenchoides fragarieae*, *Aphelenchus avenae*, *Radopholus similis*, *Tylenchulus semipenetrans*, *Rotylenchulus reniformis*, *Bursaphelenchus xylophilus*, *Helicotylenchus*, *Hoplolaimus*, *Paratrichodorus*, *Longidorus*, *Nacobbus*, *Subanquina*, *Belonolaimus*, *Criconemoides*, *Ditylenchus*, *Dolichodorus*, *Hemicriconemoides*, *Hemicycliophora*, *Hirschmanniella*, *Macroposthonia*, *Melinius*, *Punctodera*, *Quinisulcius*, *Scutellonema*, *Xiphinema*, *Tylenchorhynchus*, and *Mesocriconema*.

In the above harmful organisms, mutations within the species is not particularly limited. Namely, the weeds also include any of weeds that have a reduced sensitivity to a specific insecticide, fungicide or herbicide. The reduced sensitivity may be attributed to a mutation at a target site (target site mutations), or may be attributed to any factors other than target site mutation (non-target site mutations). The factors reducing sensitivity by non-target site mutations include metabolic enhancement, defective absorption, defective transition, and efflux out of the system, etc. A cause of the metabolic enhancement includes an enhanced activity of metabolic enzymes such as cytochrome P450 monooxygenases, aryl acylamidases, esterases and glutathione S-transferase. The efflux out of the system includes the transfer to a vacuole by an ABC transporter. Examples of the reduced sensitivity in weeds caused by the target site mutations include, for example, weeds having one or more of the following amino acid substitutions in ALS gene. Ala122Thr, Ala122Val, Ala122Tyr, Pro197Ser, Pro197His, Pro197Thr, Pro197Arg, Pro197Leu, Pro197Gln, Pro197Ala, Pro197Ile, Ala205Val, Ala205Phe, Asp376Glu, Arg377His, Trp574Leu, Trp574Gly, Trp574Met, Ser653Thr, Ser653Thr, Ser653Asn, Ser635Ile, Gly654Glu, Gly645Asp. Also, examples of the reduced sensitivity in weeds caused by the target site mutations include one or more of the following amino acid substitutions in ACCase gene. Ile1781Leu, Ile1781Val, Ile1781Thr, Trp1999Cys, Trp1999Leu, Ala2004Val, Trp2027Cys, Ile2041Asn, Ile2041Val, Asp2078Gly, Cys2088Arg, Gly2096Ala, Gly2096Ser. Further, examples of the reduced sensitivity in weedy caused by the target site mutations include ΔGly210 in PPX2L, gene and Arg98Leu mutation in PPX1 gene. In particular, the present invention can efficiently control hiyumodoki (tall waterhemp; *Amaranthus tuberculatos*) and ohonagaaogeito (Palmer amaranth; *Amaranthus palmeri*) which have ΔGly210 mutation in PPX2L gene and butakusa (common ragweed; *Ambrosia artemisiaefolia*) which has Arg98Leu in PPX1. Moreover, examples of the reduced sensitivity in weeds caused by the target site mutations include amino acid substitutions such as Thr102Ile, Pro106Ser, Pro106Ala and Pro106Leu in EPSP gene. In particular, the present invention can efficiently control glyphosate-resistant ohishiba (goosegrass; *Eleusine indica*), glyphosate-resistant nezumimugi (Italian ryegrass; *Lolium multiflorum*), glyphosate-resistant bomugi (rigid ryegrass; *Lolium rigidum*), glyphosate-resistant susukimehishiba (sourgrass; *Digitaria insularis*), glyphosate-resistant hiyumodoki (tall waterhemp; *Amaranthus tuberculatos*), and glyphosate-resistant kohimebie (jungle rice; *Echinochloa colonum*) which have one or both of the amino acid substitutions. Similarly, examples of the reduced sensitivity in weeds caused by the target site include weeds having the increased copy numbers of EPSP gene, and in particular, the present invention can efficiently control glyphosate-resistant ohonagaaogeito (Palmer amaranth; *Amaranthus palmeri*), glyphosate-resistant hiyumodoki (tall waterhemp; *Amaranthus tuberculatos*) and glyphosate-resistant hokigi (kochia; *Kochia scoparia*) which have the mutation. The present invention can also efficiently control himemukashiyomogi (marestail; *Conyza canadensis*), oarechinogiku (Guernsey fleabane; *Conyza sumatrensis*) and arechinogiku (fleabane; *Conyza bonariensis*) having the resistance to glyphosate related to ABC transporters.

In the method for controlling weeds and the present method for controlling harmful organisms of the present invention, one or more other herbicides, plant growth regulators, and safeners can be used in combination for the treatment with the compound X. The combination here may be blending, mixing, or performing sequential treatments. In a case of the sequential treatments, the order thereof is not particularly limited.

Examples of the herbicides, plant growth regulators, and safeners include the followings:

Herbicides such as glyphosate and a salt thereof (isopropylammonium salt, ammonium salt, potassium salt, guanidine salt, dimethylamine salt, or monoethanolamine salt), MCPA and a salt or an ester thereof (dimethylammonium salt, 2-ethylhexyl ester, isoctyl ester (i.e., isooctyl ester), or sodium salt), MCPB, mecoprop and a salt or an ester thereof (dimethylammonium salt, diolamine salt, ethadyl ester (i.e., 1,2-ethanediyl ester), 2-ethylhexyl ester, isoctyl ester (i.e., isooctyl ester), methyl ester, potassium salt, sodium salt, or trolamine salt), mecoprop-P and a salt or an ester thereof (dimethylammonium salt, 2-ethylhexyl ester, isobutyl salt, or potassium salt), dichlorprop and a salt or an ester thereof (butotyl ester (i.e., 2-butoxyethyl ester), dimethylammonium salt, 2-ethylhexyl ester, isoctyl ester (i.e., isooctyl ester), methyl ester, potassium salt, or sodium salt), dichlorprop-P, dichlorprop-P-dimethylammonium, quinclorac, quinmerac, bromoxynil, bromoxynil-octanoate, dichlobenil, methiozolin, ioxynil, ioxynil-octanoate, di-allate, butylate, tri-allate, phenmedipham, chlorpropham, desmedipham, asulam, phenisopham, benthiocarb, molinate, esprocarb, pyributicarb, prosulfocarb, orbencarb, EPTC, dimepiperate, swep, propachlor, metazachlor, alachlor, acetochlor, metolachlor, S-metolachlor, butachlor, pretilachlor, thenylchlor, aminocyclopyrachlor, aminocyclopyrachlor-methyl, aminocyclopyrachlor-potassium, trifluralin, pendimethalin, ethalfluralin, benfluralin, prodiamine, simazine, atrazine, propazine, cyanazine, ametryn, simetryn, dimethametryn, prometryn, indaziflam, triaziflam, metribuzin, hexazinone, terbumeton, terbuthylazine, terbutryn, trietazine, isoxaben, diflufenican, diuron, linuron, metobromuron, metoxuron, monolinuron, siduron, fluometuron, difenoxuron, methyldaimuron, isoproturon, isouron, tebuthiuron, benzthiazuron, methabenzthiazuron, propanil, mefenacet, clomeprop, naproanilide, bromobutide, daimuron, cumyluron, diflufenzopyr, etobenzanid, bentazon, tridiphane, indanofan, amitrole, fenchlorazole, clomazone, maleic hydrazide, pyridate, chloridazon, norflurazon, bromacil, terbacil, lenacil, oxaziclomefone, cinmethylin, benfuresate, cafenstrole, flufenacet, pyrithiobac, pyrithiobac-sodium, pyriminobac, pyriminobac-methyl, bispyribac, bispyribac-sodium, pyribenzoxim, pyrimisulfan, pyriftalid, triafamone, fentrazamide, dimethenamid, dimethenamid-P, ACN, dithiopyr, triclopyr and a salt or an ester thereof (butotyl ester (i.e., 2-butoxyethyl ester) or triethylammonium salt), fluroxypyr, fluroxypyr-meptyl, thiazopyr, aminopyralid and a salt or an ester thereof (potassium salt or triisopanolammonium salt), clopyralid and a salt thereof (olamine salt, potassium salt, or triethylammonium salt), picloram and a salt thereof (potassium salt or triisopanolammonium salt), dalapon, chlorthiamid, amidosulfuron, azimsulfuron, bensulfuron, bensulfuron-methyl, chlorimuron, chlorimuron-ethyl, cyclosulfamuron, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, mesosulfuron, mesosulfuron-methyl, metazosulfuron, nicosulfuron, orthosulfamuron, oxasulfuron, primisulfuron, primsulfuron-methyl, propyrisulfuron, pyrazosulfuron, pyrazosulfuron-ethyl, rimsulfuron, sulfometuron, sulfometuron-methyl, sulfosulfuron, trifloxysulfuron-sodium, trifloxysulfuron, chlorsulfuron, cinosulfuron, ethametsulfuron, ethametsulfuron-methyl, iodsulfuron, iodosulfuron-methyl-sodium, iofensulfuron, iofensulfuron-sodium, metsulfuron, metsulfuron-methyl, prosulfuron, thifensulfuron, thifensulfuron-methyl, triasulfuron, tribenuron, tribenuron-methyl, triflusulfuron, triflusulfuron-methyl, tritosulfuron, picolinafen, beflubutamid, norflurazon, fluridone, flurochloridone, flurtamone, benzobicyclon, bicyclopyrone, mesotrione, sulcotrione, tefuryltrione, tembotrione, isoxachlortole, isoxaflutole, benzofenap, pyrasulfotole, pyrazolynate, pyrazoxyfen, topramezone, tolpyralate, lancotrione-sodium, flupoxam, amicarbazone, bencarbazone, flucarbazone, flucarbazone-sodium, ipfencarbazone, propoxycarbazone, propoxycarbazone-sodium, thiencarbazone, thiencarbazone-methyl, cloransulam, cloransulam-methyl, diclosulam, florasulam, flumetsulam, metosulam, penoxsulam, pyroxsulam, imazamethabenz, imazamethabenz-methyl, imazamox, imazamox-ammonium, imazapic, imazapic-ammonium, imazapyr, imazapyr-isopropyrammonium, imazaquin, imazaquin-ammonium, imazethapyr, imazethapyr-ammonium, clodinafop, clodinafop-propargyl, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, propaquizafop, quizalofop, quizalofop-ethyl, quizalofop-P, quizalofop-P-ethyl, alloxydim, clethodim, sethoxydim, tepraloxydim, tralkoxydim, pinoxaden, fenoxasulfone, glufosinate, glufosinate-ammonium, glufosinate-P, glufosinate-P-sodium, bialaphos, anilofos, bensulide, butamifos, paraquat, paraquat-dichloride, diquat, diquat-dibromide, halauxifen, halauxifen-methyl, florpyrauxifen, florpyrauxifen-benzyl, flumioxazin, flumiclorac-pentyl, fomesafen-sodium, lactofen, saflufenacil, tiafenacil, trifludimoxazin, acifluorfen-sodium, aclonifen, bifenox, chlomethoxyfen, chlornitrofen, ethoxyfen-ethyl, fluorodifen, fluoroglycofen-ethyl, fluoronitrofen, halosafen, nitrofen, nitrofluorfen, oxyfluorfen, cinidon-ethyl, profluazol, pyraclonil, oxadiargyl, oxadiazone, pentoxazone, fluazolate, pyraflufen-ethyl, benzfendizone, butafenacil, fluthiacet-methyl, thidiazimin, azafenidin, carfentrazone-ethyl, sulfentrazone, and flufenpyr-ethyl;

Plant growth regulators such as hymexazol, paclobutrazol, uniconazole, uniconazole-P, inabenfide, prohexadione-calcium, 1-methylcyclopropene, and trinexapac; and Safeners such as benoxacor, cloquintocet, cloquintocet-mexyl, cyometrinil, cyprosulfamide, dichlormid, dicyclonon, dietholate, fenchlorazole, fenchlorazole-ethyl, fenclorim, flurazole, fluxofenim, furilazole, isoxadifen, isoxadifen-ethyl, mefenpyr, mefenpyr-diethyl, mephenate, naphthalic anhydride, and oxabetrinil.

In the present invention, preferred examples of the herbicides which can be used simultaneously in combination with the compound X include glyphosate potassium salt, glyphosate guanidine salt, glyphosate dimethylamine salt, glyphosate monoethanolamine salt, glyphosinate ammonium salt, glyphosate isopropylammonium salt, flumioxazin, flumiclorac-pentyl, clethodim, lactofen, S-metolachlor, metribuzin, fulfenacet, nicosulfuron, rimsulfuron, acetochlor, mesotrione, isoxaflutole, chlosimuron-ethyl, thifensulfuron-methyl, cloransulam-methyl, imazethapyr ammonium salt, and metribuzin.

In the present invention, preferred examples of the safeness which can be used simultaneously in combination with the compound X include cyprosulfamide, benoxacor, dichlormid, and furilazole.

Examples of combinations of the compound X with herbicides and/or safeness are described below, but the examples are not limited thereto. The ratio of the compound to be combined with the compound X is usually in a range of 0.01 to 1,000 times, preferably in a range of 0.1 to 100 times, and more preferably in a range of 1 to 10 times on a part by weight basis, as opposed to the amount of the compound X.

Combination of the compound X and quinchlorac;
Combination of the compound X and quinmerac;
Combination of the compound X and bromoxynil;
Combination of the compound X and bromoxynil-octanoate;
Combination of the compound X and dichlobenil;
Combination of the compound X and methiozolin;
Combination of the compound X and ioxynil;
Combination of the compound X and ioxynil-octanoate;
Combination of the compound X and di-allate;
Combination of the compound X and butylate;
Combination of the compound X and tri-allate;
Combination of the compound X and phenmedipham;
Combination of the compound X and chlorpropham;
Combination of the compound X and desmedipham;
Combination of the compound X and asulam;
Combination of the compound X and phenisopham;
Combination of the compound X and benthiocarb;
Combination of the compound X and molinate;
Combination of the compound X and esprocarb;
Combination of the compound X and pyributicarb;
Combination of the compound X and prosulfocarb;
Combination of the compound X and orbencarb;
Combination of the compound X and EPTC;
Combination of the compound X and dimepiperate;
Combination of the compound X and swep;
Combination of the compound X and propachlor;
Combination of the compound X and metazachlor;
Combination of the compound X and alachlor;
Combination of the compound X and acetochlor;
Combination of the compound X and metolachlor;
Combination of the compound X and S-metolachlor;
Combination of the compound X and butachlor;
Combination of the compound X and pretilachlor;
Combination of the compound X and thenylchlor;
Combination of the compound X and aminocyclopyrachlor;
Combination of the compound X and aminocyclopyrachlor-methyl;
Combination of the compound X and aminocyclopyrachlor-potassium;
Combination of the compound X and trifluralin;
Combination of the compound X and pendimethalin;
Combination of the compound X and ethalfluralin;
Combination of the compound X and benfluralin;
Combination of the compound X and prodiamine;
Combination of the compound X and simazine;
Combination of the compound X and atrazine;
Combination of the compound X and propazine;
Combination of the compound X and cyanazine;
Combination of the compound X and ametryn;
Combination of the compound X and simetryn;
Combination of the compound X and dimethametryn;
Combination of the compound X and indaziflam;
Combination of the compound X and triaziflam;
Combination of the compound X and metribuzin;
Combination of the compound X and hexazinone;
Combination of the compound X and terbumeton;
Combination of the compound X and terbuthylazine;
Combination of the compound X and terbutryn;
Combination of the compound X and trietazine;
Combination of the compound X and isoxaben;
Combination of the compound X and diflufenican;
Combination of the compound X and diuron;
Combination of the compound X and linuron;
Combination of the compound X and metobromuron;
Combination of the compound X and metoxuron;
Combination of the compound X and monolinuron;
Combination of the compound X and siduron;
Combination of the compound X and fluometuron;
Combination of the compound X and difenoxuron;
Combination of the compound X and methyl-daimuron;
Combination of the compound X and isoproturon;
Combination of the compound X and isouron;
Combination of the compound X and tebuthiuron;
Combination of the compound X and benzthiazuron;
Combination of the compound X and methabenzthiazuron;
Combination of the compound X and propanil;
Combination of the compound X and mefenacet;
Combination of the compound X and clomeprop;
Combination of the compound X and naproanilide;
Combination of the compound X and bromobutide;
Combination of the compound X and daimuron;
Combination of the compound X and cumyluron;
Combination of the compound X and diflufenzopyr;
Combination of the compound X and etobenzanid;
Combination of the compound X and bentazon;
Combination of the compound X and tridiphane;
Combination of the compound X and indanofan;
Combination of the compound X and amitrole;
Combination of the compound X and fenchlorazole-ethyl;
Combination of the compound X and mefenpyr-diethyl;
Combination of the compound X and benoxacor;
Combination of the compound X and dichlormid;
Combination of the compound X and cloquintocet-mexyl;
Combination of the compound X and cyprosulfamide;
Combination of the compound X and isoxadifen-ethyl;
Combination of the compound X and clomazone;
Combination of the compound X and maleic hydrazide;
Combination of the compound X and pyridate;
Combination of the compound X and chloridazon;
Combination of the compound X and bromacil;
Combination of the compound X and terbacil;
Combination of the compound X and lenacil;
Combination of the compound X and oxaziclomefone;
Combination of the compound X and cinmethylin;
Combination of the compound X and benfuresate;
Combination of the compound X and cafenstrole;
Combination of the compound X and flufenacet;
Combination of the compound X and pyrithiobac;
Combination of the compound X and pyrithiobac-sodium;
Combination of the compound X and pyriminobac;
Combination of the compound X and pyriminobac-methyl;
Combination of the compound X and bispyribac;
Combination of the compound X and bispyribac-sodium;
Combination of the compound X and pyribenzoxim;
Combination of the compound X and pyrimisulfan;
Combination of the compound X and pyriftalid;
Combination of the compound X and triafamone;
Combination of the compound X and fentrazamide;
Combination of the compound X and dimethenamid;
Combination of the compound X and dimethenamid-P;
Combination of the compound X and ACN;
Combination of the compound X and dithiopyr;
Combination of the compound X and triclopyr;
Combination of the compound X and triclopyr-butotyl;
Combination of the compound X and triclopyr ammonium salt;
Combination of the compound X and fluroxypyr;

Combination of the compound X and fluroxypyr-meptyl;
Combination of the compound X and thiazopyr;
Combination of the compound X and aminopyralid;
Combination of the compound X and aminopyralid potassium salt;
Combination of the compound X and aminopyralid tri-isopanol ammonium salt;
Combination of the compound X and clopyralid olamine salt;
Combination of the compound X and clopyralid potassium salt;
Combination of the compound X and clopyralid triethyl ammonium salt;
Combination of the compound X and picloram potassium salt;
Combination of the compound X and picloram triisopanol ammonium salt;
Combination of the compound X and dalapon;
Combination of the compound X and chlorthiamid;
Combination of the compound X and amidosulfuron;
Combination of the compound X and azimsulfuron;
Combination of the compound X and bensulfuron-methyl;
Combination of the compound X and chlorimuron-ethyl;
Combination of the compound X and cyclosulfamuron;
Combination of the compound X and ethoxysulfuron;
Combination of the compound X and flazasulfuron;
Combination of the compound X and flucetosulfuron;
Combination of the compound X and flupyrsulfuron-methyl-sodium;
Combination of the compound X and foramsulfuron
Combination of the compound X and halosulfuron-methyl;
Combination of the compound X and imazosulfuron;
Combination of the compound X and mesosulfuron-methyl;
Combination of the compound X and metazosulfuron;
Combination of the compound X and nicosulfuron;
Combination of the compound X and orthosulfamuron;
Combination of the compound X and oxasulfuron;
Combination of the compound X and primisulfuron-methyl;
Combination of the compound X and propyrisulfuron;
Combination of the compound X and pyrazosulfuron-ethyl;
Combination of the compound X and rimsulfuron;
Combination of the compound X and sulfometuron-methyl;
Combination of the compound X and sulfosulfuron;
Combination of the compound X and trifloxysulfuron-sodium salt;
Combination of the compound X and chlorsulfuron;
Combination of the compound X and cinosulfuron;
Combination of the compound X and ethametsulfuron;
Combination of the compound X and iodosulfuron-methyl-sodium;
Combination of the compound X and iofensulfuron-sodium;
Combination of the compound X and metsulfuron-methyl;
Combination of the compound X and prosulfuron;
Combination of the compound X and thifensulfuron-methyl;
Combination of the compound X and triasulfuron;
Combination of the compound X and tribenuron-methyl;
Combination of the compound X and triflusulfuron-methyl;
Combination of the compound X and tritosulfuron;
Combination of the compound X and picolinafen;
Combination of the compound X and beflubutamid;
Combination of the compound X and norflurazon;
Combination of the compound X and fluridone;
Combination of the compound X and flurochloridone;
Combination of the compound X and flurtamone;
Combination of the compound X and benzobicyclon;
Combination of the compound X and bicyclopyrone;
Combination of the compound X and mesotrione;
Combination of the compound X and sulcotrione;
Combination of the compound X and tefuryltrione;
Combination of the compound X and tembotrione;
Combination of the compound X and isoxachlortole;
Combination of the compound X and isoxaflutole;
Combination of the compound X and benzofenap;
Combination of the compound X and pyrasulfotole;
Combination of the compound X and pyrazolynate;
Combination of the compound X and pyrazoxyfen;
Combination of the compound X and topramezone;
Combination of the compound X and tolpyralate;
Combination of the compound X and lancotrione-sodium;
Combination of the compound X and flupoxam;
Combination of the compound X and amicarbazone;
Combination of the compound X and bencarbazone;
Combination of the compound X and flucarbazone-sodium salt;
Combination of the compound X and ipfencarbazone;
Combination of the compound X and propoxycarbazone-sodium salt;
Combination of the compound X and thiencarbazone-methyl;
Combination of the compound X and cloransulam-methyl;
Combination of the compound X and diclosulam;
Combination of the compound X and florasulam;
Combination of the compound X and flumetsulam;
Combination of the compound X and metosulam;
Combination of the compound X and penoxsulam;
Combination of the compound X and pyroxsulam;
Combination of the compound X and imazamethabenz-methyl;
Combination of the compound X and imazamox-ammonium salt;
Combination of the compound X and imazapic-ammonium;
Combination of the compound X and imazapyr isopropyl ammonium salt;
Combination of the compound X and imazaquin-ammonium salt;
Combination of the compound X and imazethapyr-ammonium salt;
Combination of the compound X and clodinafop-propargyl;
Combination of the compound X and cyhalofop-butyl;
Combination of the compound X and diclofop-methyl;
Combination of the compound X and fenoxaprop-ethyl;
Combination of the compound X and fenoxaprop-P-ethyl;
Combination of the compound X and fluazifop-butyl;
Combination of the compound X and fluazifop-P-butyl;
Combination of the compound X and haloxyfop-methyl;
Combination of the compound X and haloxyfop-P-methyl;
Combination of the compound X and propaquizafop;
Combination of the compound X and quizalofop-ethyl;
Combination of the compound X and quizalofop-P-ethyl;
Combination of the compound X and alloxydim;

Combination of the compound X and clethodim;
Combination of the compound X and sethoxydim;
Combination of the compound X and tepraloxydim;
Combination of the compound X and tralkoxydim;
Combination of the compound X and pinoxaden;
Combination of the compound X and fenoxasulfone;
Combination of the compound X and glufosinate;
Combination of the compound X and glufosinate-ammonium salt;
Combination of the compound X and glufosinate-P;
Combination of the compound X and glufosinate-P-sodium salt;
Combination of the compound X and bialaphos;
Combination of the compound X and anilofos;
Combination of the compound X and bensulide;
Combination of the compound X and butamifos;
Combination of the compound X and paraquat;
Combination of the compound X and paraquat-dichloride;
Combination of the compound X and diquat;
Combination of the compound X and diquat-dibromide;
Combination of the compound X and halauxifen;
Combination of the compound X and halauxifen-methyl;
Combination of the compound X and florpyrauxifen;
Combination of the compound X and florpyrauxifen-benzyl;
Combination of the compound X and flumioxazin;
Combination of the compound X and flumiclorac-pentyl;
Combination of the compound X and fomesafen-sodium salt;
Combination of the compound X and lactofen;
Combination of the compound X and saflufenacil;
Combination of the compound X and tiafenacil;
Combination of the compound X and trifludimoxazin;
Combination of the compound X and acifluorfen-sodium salt;
Combination of the compound X and aclonifen;
Combination of the compound X and bifenox;
Combination of the compound X and chlomethoxyfen;
Combination of the compound X and chlornitrofen;
Combination of the compound X and ethoxyfen-ethyl;
Combination of the compound X and fluorodifen;
Combination of the compound X and fluoroglycofen-ethyl;
Combination of the compound X and fluoronitrofen;
Combination of the compound X and halosafen;
Combination of the compound X and nitrofen;
Combination of the compound X and nitrofluorfen;
Combination of the compound X and oxyfluorfen;
Combination of the compound X and cinidon-ethyl;
Combination of the compound X and profluazol;
Combination of the compound X and pyraclonil;
Combination of the compound X and oxadiargyl;
Combination of the compound X and oxadiazone;
Combination of the compound X and pentoxazone;
Combination of the compound X and fluazolate;
Combination of the compound X and pyraflufen-ethyl;
Combination of the compound X and benzfendizone;
Combination of the compound X and butafenacil;
Combination of the compound X and fluthiacet-methyl;
Combination of the compound X and thidiazimin;
Combination of the compound X and azafenidin;
Combination of the compound X and carfentrazone-ethyl;
Combination of the compound X and sulfentrazone;
Combination of the compound X and flufenpyr-ethyl;
Combination of the compound X and glyphosate;
Combination of the compound X and glyphosate isopropylammonium salt;
Combination of the compound X and glyphosate ammonium salt;
Combination of the compound X and glyphosate potassium salt;
Combination of the compound X and glyphosatse guanidine salt;
Combination of the compound X and glyphosate dimethylamine salt;
Combination of the compound X and glyphosate monoethanolamine salt;
Combination of the compound X and MCPA;
Combination of the compound X and MCPA dimethylammonium salt;
Combination of the compound X and MCPA 2-ethylhexyl ester;
Combination of the compound X and MCPA isoctyl;
Combination of the compound X and MCPA sodium salt;
Combination of the compound X and MCPB;
Combination of the compound X and mecoprop;
Combination of the compound X and mecoprop dimethyl ammonium salt;
Combination of the compound X and mecoprop diolamine salt;
Combination of the compound X and mecoprop ethadyl;
Combination of the compound X and mecoprop 2-ethylhexyl ester;
Combination of the compound X and mecoprop isoctyl;
Combination of the compound X and mecoprop methyl ester;
Combination of the compound X and mecoprop potassium salt;
Combination of the compound X and mecoprop sodium salt;
Combination of the compound X and mecoprop trolamine salt;
Combination of the compound X and mecoprop P;
Combination of the compound X and mecoprop P dimethylammonium salt;
Combination of the compound X and mecoprop P 2-ethylhexyl ester;
Combination of the compound X and mecoprop P isobutyl ester;
Combination of the compound X and mecoprop P potassium salt;
Combination of the compound X and dichlorprop;
Combination or the compound X and dichlorprop butotyl
Combination of the compound X and dichlorprop dimethyl ammonium salt;
Combination of the compound X and dichlorprop 2-ethylhexyl ester;
Combination of the compound X and dichlorprop isoctyl;
Combination of the compound X and dichlorprop methyl ester;
Combination of the compound X and dichlorprop potassium salt;
Combination of the compound X and dichlorprop sodium salt;
Combination of the compound X and dichlorprop P;
Combination of the compound X and dichlorprop P dimethyl ammonium salt;

In the present method for controlling harmful organisms, examples of combinations in a case where the number of compounds A used to treat the crop seeds is two or more are listed in following Tables 1 to 3, but the examples are not limited thereto.

TABLE 1

| Combination No. | Combination of compounds | |
|---|---|---|
| 1-1 | Clothianidin | Ipconazole |
| 1-2 | Clothianidin | Metconazole |
| 1-3 | Clothianidin | Difenoconazole |
| 1-4 | Clothianidin | Tebuconazole |
| 1-5 | Clothianidin | Prothioconazole |
| 1-6 | Clothianidin | Fluquinconazole |
| 1-7 | Clothianidin | Triticonazole |
| 1-8 | Clothianidin | Imazalil |
| 1-9 | Clothianidin | Pencycuron |
| 1-10 | Clothianidin | Prochloraz |
| 1-11 | Clothianidin | Pyraclostrobin |
| 1-12 | Clothianidin | Azoxystrobin |
| 1-13 | Clothianidin | Trifloxystrobin |
| 1-14 | Clothianidin | Metalaxyl |
| 1-15 | Clothianidin | Metalaxyl-M |
| 1-16 | Clothianidin | Fludioxonil |
| 1-17 | Clothianidin | Thiram |
| 1-18 | Clothianidin | Mancozeb |
| 1-19 | Clothianidin | Flutolanil |
| 1-20 | Clothianidin | Sedaxane |
| 1-21 | Clothianidin | Penflufen |
| 1-22 | Clothianidin | Fluxapyroxad |
| 1-23 | Clothianidin | *Bacillus firmus* |
| 1-24 | Clothianidin | *Pasteuria penetrans* |
| 1-25 | Clothianidin | Abamectin |
| 1-26 | Clothianidin | Thiodicarb |
| 1-27 | Clothianidin | Tolclofos-methyl |
| 1-28 | Clothianidin | Ethaboxam |
| 1-29 | Clothianidin | Compound 1 |
| 1-30 | Clothianidin | Mandestrobin |
| 1-31 | Clothianidin | Compound 2 |
| 1-32 | Clothianidin | Orysastrobin |
| 1-33 | Clothianidin | Isotianil |
| 1-34 | Clothianidin | Probenazole |
| 1-35 | Clothianidin | Diclocymet |
| 1-36 | Clothianidin | Furametpyr |
| 1-37 | Imidacloprid | Ipconazole |
| 1-38 | Imidacloprid | Metconazole |
| 1-39 | Imidacloprid | Difenoconazole |
| 1-40 | Imidacloprid | Tebuconazole |
| 1-41 | Imidacloprid | Prothioconazole |
| 1-42 | Imidacloprid | Fluquinconazole |
| 1-43 | Imidacloprid | Triticonazole |
| 1-44 | Imidacloprid | Imazalil |
| 1-45 | Imidacloprid | Pencycuron |
| 1-46 | Imidacloprid | Prochloraz |
| 1-47 | Imidacloprid | Pyraclostrobin |
| 1-48 | Imidacloprid | Azoxystrobin |
| 1-49 | Imidacloprid | Trifloxystrobin |
| 1-50 | Imidacloprid | Metalaxyl |
| 1-51 | Imidacloprid | Metalaxyl-M |
| 1-52 | Imidacloprid | Fludioxonil |
| 1-53 | Imidacloprid | Thiram |
| 1-54 | Imidacloprid | Mancozeb |
| 1-55 | Imidacloprid | Flutolanil |
| 1-56 | Imidacloprid | Sedaxane |
| 1-57 | Imidacloprid | Penflufen |
| 1-58 | Imidacloprid | Fluxapyroxad |
| 1-59 | Imidacloprid | *Bacillus firmus* |
| 1-60 | Imidacloprid | *Pasteuria penetrans* |
| 1-61 | Imidacloprid | Abamectin |
| 1-62 | Imidacloprid | Thiodicarb |
| 1-63 | Imidacloprid | Tolclofos-methyl |
| 1-64 | Imidacloprid | Ethaboxam |
| 1-65 | Imidacloprid | Compound 1 |
| 1-66 | Imidacloprid | Mandestrobin |
| 1-67 | Imidacloprid | Compound 2 |
| 1-68 | Imidacloprid | Orysastrobin |
| 1-69 | Imidacloprid | Isotianil |
| 1-70 | Imidacloprid | Probenazole |
| 1-71 | Imidacloprid | Diclocymet |
| 1-72 | Imidacloprid | Furametpyr |
| 1-73 | Thiamethoxam | Ipconazole |
| 1-74 | Thiamethoxam | Metconazole |
| 1-75 | Thiamethoxam | Difenoconazole |
| 1-76 | Thiamethoxam | Tebuconazole |
| 1-77 | Thiamethoxam | Prothioconazole |
| 1-78 | Thiamethoxam | Fluquinconazole |
| 1-79 | Thiamethoxam | Triticonazole |
| 1-80 | Thiamethoxam | Imazalil |
| 1-81 | Thiamethoxam | Pencycuron |
| 1-82 | Thiamethoxam | Prochloraz |
| 1-83 | Thiamethoxam | Pyraclostrobin |
| 1-84 | Thiamethoxam | Azoxystrobin |
| 1-85 | Thiamethoxam | Trifloxystrobin |
| 1-86 | Thiamethoxam | Metalaxyl |
| 1-87 | Thiamethoxam | Metalaxyl-M |
| 1-88 | Thiamethoxam | Fludioxonil |
| 1-89 | Thiamethoxam | Thiram |
| 1-90 | Thiamethoxam | Mancozeb |
| 1-91 | Thiamethoxam | Flutolanil |
| 1-92 | Thiamethoxam | Sedaxane |
| 1-93 | Thiamethoxam | Penflufen |
| 1-94 | Thiamethoxam | Fluxapyroxad |
| 1-95 | Thiamethoxam | *Bacillus firmus* |
| 1-96 | Thiamethoxam | *Pasteuria penetrans* |
| 1-97 | Thiamethoxam | Abamectin |
| 1-98 | Thiamethoxam | Thiodicarb |
| 1-99 | Thiamethoxam | Tolclofos-methyl |
| 1-100 | Thiamethoxam | Ethaboxam |
| 1-101 | Thiamethoxam | Compound 1 |
| 1-102 | Thiamethoxam | Mandestrobin |
| 1-103 | Thiamethoxam | Compound 2 |
| 1-104 | Thiamethoxam | Orysastrobin |
| 1-105 | Thiamethoxam | Isotianil |
| 1-106 | Thiamethoxam | Probenazole |
| 1-107 | Thiamethoxam | Diclocymet |
| 1-108 | Thiamethoxam | Furametpyr |
| 1-109 | Beta-cyfluthrin | Ipconazole |
| 1-110 | Beta-cyfluthrin | Metconazole |
| 1-111 | Beta-cyfluthrin | Difenoconazole |
| 1-112 | Beta-cyfluthrin | Tebuconazole |
| 1-113 | Beta-cyfluthrin | Prothioconazole |
| 1-114 | Beta-cyfluthrin | Fluquinconazole |
| 1-115 | Beta-cyfluthrin | Triticonazole |
| 1-116 | Beta-cyfluthrin | Imazalil |
| 1-117 | Beta-cyfluthrin | Pencycuron |
| 1-118 | Beta-cyfluthrin | Prochloraz |
| 1-119 | Beta-cyfluthrin | Pyraclostrobin |
| 1-120 | Beta-cyfluthrin | Azoxystrobin |
| 1-121 | Beta-cyfluthrin | Trifloxystrobin |
| 1-122 | Beta-cyfluthrin | Metalaxyl |
| 1-123 | Beta-cyfluthrin | Metalaxyl-M |
| 1-124 | Beta-cyfluthrin | Fludioxonil |
| 1-125 | Beta-cyfluthrin | Thiram |
| 1-126 | Beta-cyfluthrin | Mancozeb |
| 1-127 | Beta-cyfluthrin | Flutolanil |
| 1-128 | Beta-cyfluthrin | Sedaxane |
| 1-129 | Beta-cyfluthrin | Penflufen |
| 1-130 | Beta-cyfluthrin | Fluxapyroxad |
| 1-131 | Beta-cyfluthrin | *Bacillus firmus* |
| 1-132 | Beta-cyfluthrin | *Pasteuria penetrans* |
| 1-133 | Beta-cyfluthrin | Abamectin |
| 1-134 | Beta-cyfluthrin | Thiodicarb |
| 1-135 | Beta-cyfluthrin | Tolclofos-methyl |
| 1-136 | Beta-cyfluthrin | Ethaboxam |
| 1-137 | Beta-cyfluthrin | Compound 1 |
| 1-138 | Beta-cyfluthrin | Mandestrobin |
| 1-139 | Beta-cyfluthrin | Compound 2 |
| 1-140 | Abamectin | Ipconazole |
| 1-141 | Abamectin | Metconazole |
| 1-142 | Abamectin | Difenoconazole |
| 1-143 | Abamectin | Tebuconazole |
| 1-144 | Abamectin | Prothioconazole |
| 1-145 | Abamectin | Fluquinconazole |
| 1-146 | Abamectin | Triticonazole |
| 1-147 | Abamectin | Imazalil |
| 1-148 | Abamectin | Pencycuron |
| 1-149 | Abamectin | Prochloraz |
| 1-150 | Abamectin | Pyraclostrobin |
| 1-151 | Abamectin | Azoxystrobin |
| 1-152 | Abamectin | Trifloxystrobin |
| 1-153 | Abamectin | Metalaxyl |
| 1-154 | Abamectin | Metalaxyl-M |
| 1-155 | Abamectin | Fludioxonil |
| 1-156 | Abamectin | Thiram |

TABLE 1-continued

| Combination No. | Combination of compounds | |
|---|---|---|
| 1-157 | Abamectin | Mancozeb |
| 1-158 | Abamectin | Flutolanil |
| 1-159 | Abamectin | Sedaxane |
| 1-160 | Abamectin | Penflufen |
| 1-161 | Abamectin | Fluxapyroxad |
| 1-162 | Abamectin | Bacillus firmus |
| 1-163 | Abamectin | Pasteuria penetrans |
| 1-164 | Abamectin | Thiodicarb |
| 1-165 | Abamectin | Tolclofos-methyl |
| 1-166 | Abamectin | Ethaboxam |
| 1-167 | Abamectin | Compound 1 |
| 1-168 | Abamectin | Mandestrobin |
| 1-169 | Abamectin | Compound 2 |
| 1-170 | Thiodicarb | Ipconazole |
| 1-171 | Thiodicarb | Metconazole |
| 1-172 | Thiodicarb | Difenoconazole |
| 1-173 | Thiodicarb | Tebuconazole |
| 1-174 | Thiodicarb | Prothioconazole |
| 1-175 | Thiodicarb | Fluquinconazole |
| 1-176 | Thiodicarb | Triticonazole |
| 1-177 | Thiodicarb | Imazalil |
| 1-178 | Thiodicarb | Pencycuron |
| 1-179 | Thiodicarb | Prochloraz |
| 1-180 | Thiodicarb | Pyraclostrobin |
| 1-181 | Thiodicarb | Azoxystrobin |
| 1-182 | Thiodicarb | Trifloxystrobin |
| 1-183 | Thiodicarb | Metalaxyl |
| 1-184 | Thiodicarb | Metalaxyl-M |
| 1-185 | Thiodicarb | Fludioxonil |
| 1-186 | Thiodicarb | Thiram |
| 1-187 | Thiodicarb | Mancozeb |
| 1-188 | Thiodicarb | Flutolanil |
| 1-189 | Thiodicarb | Sedaxane |
| 1-190 | Thiodicarb | Penflufen |
| 1-191 | Thiodicarb | Fluxapyroxad |
| 1-192 | Thiodicarb | Bacillus firmus |
| 1-193 | Thiodicarb | Pasteuria penetrans |
| 1-194 | Thiodicarb | Tolclofos-methyl |
| 1-195 | Thiodicarb | Ethaboxam |
| 1-196 | Thiodicarb | Compound 1 |
| 1-197 | Thiodicarb | Mandestrobin |
| 1-198 | Thiodicarb | Compound 2 |
| 1-199 | Thiodicarb | Furametpyr |
| 1-200 | Metalaxyl | Ipconazole |
| 1-201 | Metalaxyl | Metconazole |
| 1-202 | Metalaxyl | Difenoconazole |
| 1-203 | Metalaxyl | Tebuconazole |
| 1-204 | Metalaxyl | Prothioconazole |
| 1-205 | Metalaxyl | Fluquinconazole |
| 1-206 | Metalaxyl | Triticonazole |
| 1-207 | Metalaxyl | Imazalil |
| 1-208 | Metalaxyl | Pencycuron |
| 1-209 | Metalaxyl | Prochloraz |
| 1-210 | Metalaxyl | Pyraclostrobin |
| 1-211 | Metalaxyl | Azoxystrobin |
| 1-212 | Metalaxyl | Trifloxystrobin |
| 1-213 | Metalaxyl | Fludioxonil |
| 1-214 | Metalaxyl | Thiram |
| 1-215 | Metalaxyl | Flutolanil |
| 1-216 | Metalaxyl | Sedaxane |
| 1-217 | Metalaxyl | Penflufen |
| 1-218 | Metalaxyl | Fluxapyroxad |
| 1-219 | Metalaxyl | Bacillus firmus |
| 1-220 | Metalaxyl | Pasteuria penetrans |
| 1-221 | Metalaxyl | Tolclofos-methyl |
| 1-222 | Metalaxyl | Ethaboxam |
| 1-223 | Metalaxyl | Compound 1 |
| 1-224 | Metalaxyl | Mandestrobin |
| 1-225 | Metalaxyl | Compound 2 |
| 1-226 | Metalaxyl | Furametpyr |
| 1-227 | Metalaxyl-M | Ipconazole |
| 1-228 | Metalaxyl-M | Metconazole |
| 1-229 | Metalaxyl-M | Difenoconazole |
| 1-230 | Metalaxyl-M | Tebuconazole |
| 1-231 | Metalaxyl-M | Prothioconazole |
| 1-232 | Metalaxyl-M | Fluquinconazole |
| 1-233 | Metalaxyl-M | Triticonazole |
| 1-234 | Metalaxyl-M | Imazalil |
| 1-235 | Metalaxyl-M | Pencycuron |
| 1-236 | Metalaxyl-M | Prochloraz |
| 1-237 | Metalaxyl-M | Pyraclostrobin |
| 1-238 | Metalaxyl-M | Azoxystrobin |
| 1-239 | Metalaxyl-M | Trifloxystrobin |
| 1-240 | Metalaxyl-M | Fludioxonil |
| 1-241 | Metalaxyl-M | Thiram |
| 1-242 | Metalaxyl-M | Flutolanil |
| 1-243 | Metalaxyl-M | Sedaxane |
| 1-244 | Metalaxyl-M | Penflufen |
| 1-245 | Metalaxyl-M | Fluxapyroxad |
| 1-246 | Metalaxyl-M | Bacillus firmus |
| 1-247 | Metalaxyl-M | Pasteuria penetrans |
| 1-248 | Metalaxyl-M | Tolclofos-methyl |
| 1-249 | Metalaxyl-M | Ethaboxam |
| 1-250 | Metalaxyl-M | Compound 1 |
| 1-251 | Metalaxyl-M | Mandestrobin |
| 1-252 | Metalaxyl-M | Compound 2 |
| 1-253 | Metalaxyl-M | Furametpyr |
| 1-254 | Fludioxonil | Ipconazole |
| 1-255 | Fludioxonil | Metconazole |
| 1-256 | Fludioxonil | Difenoconazole |
| 1-257 | Fludioxonil | Tebuconazole |
| 1-258 | Fludioxonil | Prothioconazole |
| 1-259 | Fludioxonil | Fluquinconazole |
| 1-260 | Fludioxonil | Triticonazole |
| 1-261 | Fludioxonil | Imazalil |
| 1-262 | Fludioxonil | Pencycuron |
| 1-263 | Fludioxonil | Prochloraz |
| 1-264 | Fludioxonil | Pyraclostrobin |
| 1-265 | Fludioxonil | Azoxystrobin |
| 1-266 | Fludioxonil | Trifloxystrobin |
| 1-267 | Fludioxonil | Thiram |
| 1-268 | Fludioxonil | Flutolanil |
| 1-269 | Fludioxonil | Sedaxane |
| 1-270 | Fludioxonil | Penflufen |
| 1-271 | Fludioxonil | Fluxapyroxad |
| 1-272 | Fludioxonil | Bacillus firmus |
| 1-273 | Fludioxonil | Pasteuria penetrans |
| 1-274 | Fludioxonil | Tolclofos-methyl |
| 1-275 | Fludioxonil | Ethaboxam |
| 1-276 | Fludioxonil | Compound 1 |
| 1-277 | Fludioxonil | Mandestrobin |
| 1-278 | Fludioxonil | Compound 2 |
| 1-279 | Fludioxonil | Furametpyr |
| 1-280 | Ipconazole | Pyraclostrobin |
| 1-281 | Ipconazole | Azoxystrobin |
| 1-282 | Ipconazole | Trifloxystrobin |
| 1-283 | Ipconazole | Thiram |
| 1-284 | Ipconazole | Flutolanil |
| 1-285 | Ipconazole | Sedaxane |
| 1-286 | Ipconazole | Penflufen |
| 1-287 | Ipconazole | Fluxapyroxad |
| 1-288 | Ipconazole | Bacillus firmus |
| 1-289 | Ipconazole | Pasteuria penetrans |
| 1-290 | Ipconazole | Tolclofos-methyl |
| 1-291 | Ipconazole | Ethaboxam |
| 1-292 | Ipconazole | Compound 1 |
| 1-293 | Ipconazole | Mandestrobin |
| 1-294 | Ipconazole | Compound 2 |
| 1-295 | Metconazole | Pyraclostrobin |
| 1-296 | Metconazole | Azoxystrobin |
| 1-297 | Metconazole | Trifloxystrobin |
| 1-298 | Metconazole | Thiram |
| 1-299 | Metconazole | Flutolanil |
| 1-300 | Metconazole | Sedaxane |
| 1-301 | Metconazole | Penflufen |
| 1-302 | Metconazole | Fluxapyroxad |
| 1-303 | Metconazole | Bacillus firmus |
| 1-304 | Metconazole | Pasteuria penetrans |
| 1-305 | Metconazole | Tolclofos-methyl |
| 1-306 | Metconazole | Ethaboxam |
| 1-307 | Metconazole | Compound 1 |
| 1-308 | Metconazole | Mandestrobin |
| 1-309 | Metconazole | Compound 2 |
| 1-310 | Difenoconazole | Pyraclostrobin |
| 1-311 | Difenoconazole | Azoxystrobin |
| 1-312 | Difenoconazole | Trifloxystrobin |

TABLE 1-continued

| Combination No. | Combination of compounds | |
|---|---|---|
| 1-313 | Difenoconazole | Thiram |
| 1-314 | Difenoconazole | Flutolanil |
| 1-315 | Difenoconazole | Sedaxane |
| 1-316 | Difenoconazole | Penflufen |
| 1-317 | Difenoconazole | Fluxapyroxad |
| 1-318 | Difenoconazole | *Bacillus firmus* |
| 1-319 | Difenoconazole | *Pasteuria penetrans* |
| 1-320 | Difenoconazole | Tolclofos-methyl |
| 1-321 | Difenoconazole | Ethaboxam |
| 1-322 | Difenoconazole | Compound 1 |
| 1-323 | Difenoconazole | Mandestrobin |
| 1-324 | Difenoconazole | Compound 2 |
| 1-325 | Prothioconazole | Pyraclostrobin |
| 1-326 | Prothioconazole | Azoxystrobin |
| 1-327 | Prothioconazole | Trifloxystrobin |
| 1-328 | Prothioconazole | Thiram |
| 1-329 | Prothioconazole | Flutolanil |
| 1-330 | Prothioconazole | Sedaxane |
| 1-331 | Prothioconazole | Penflufen |
| 1-332 | Prothioconazole | Fluxapyroxad |
| 1-333 | Prothioconazole | *Bacillus firmus* |
| 1-334 | Prothioconazole | *Pasteuria penetrans* |
| 1-335 | Prothioconazole | Tolclofos-methyl |
| 1-336 | Prothioconazole | Ethaboxam |
| 1-337 | Prothioconazole | Compound 1 |
| 1-338 | Prothioconazole | Mandestrobin |
| 1-339 | Prothioconazole | Compound 2 |
| 1-340 | Fipronil | Tefluthrin |
| 1-341 | Imidacloprid | Tefluthrin |
| 1-342 | Carboxin | Thiram |
| 1-343 | Pyraclostrobin | Fluxapyroxad |
| 1-344 | Flutolanil | Mancozeb |
| 1-345 | Fluquinconazole | Prochloraz |

TABLE 2

| Combination No. | Combination of compounds | |
|---|---|---|
| 2-1 | 1-14 | Pyraclostrobin |
| 2-2 | 1-14 | Azoxystrobin |
| 2-3 | 1-14 | Trifloxystrobin |
| 2-4 | 1-14 | Mandestrobin |
| 2-5 | 1-14 | Metconazole |
| 2-6 | 1-14 | Prothioconazole |
| 2-7 | 1-14 | Triticonazole |
| 2-8 | 1-14 | Tebuconazole |
| 2-9 | 1-14 | Difenoconazole |
| 2-10 | 1-14 | Ipconazole |
| 2-11 | 1-14 | Thiophanate-methyl |
| 2-12 | 1-14 | Fludioxonil |
| 2-13 | 1-14 | Tolclofos-methyl |
| 2-14 | 1-14 | Thiram |
| 2-15 | 1-14 | Captan |
| 2-16 | 1-14 | Carboxin |
| 2-17 | 1-14 | Boscalid |
| 2-18 | 1-14 | Thiabendazole |
| 2-19 | 1-14 | Ethaboxam |
| 2-20 | 1-15 | Pyraclostrobin |
| 2-21 | 1-15 | Azoxystrobin |
| 2-22 | 1-15 | Trifloxystrobin |
| 2-23 | 1-15 | Mandestrobin |
| 2-24 | 1-15 | Metconazole |

TABLE 2-continued

| Combination No. | Combination of compounds | |
|---|---|---|
| 2-25 | 1-15 | Prothioconazole |
| 2-26 | 1-15 | Triticonazole |
| 2-27 | 1-15 | Tebuconazole |
| 2-28 | 1-15 | Difenoconazole |
| 2-29 | 1-15 | Ipconazole |
| 2-30 | 1-15 | Thiophanate-methyl |
| 2-31 | 1-15 | Fludioxonil |
| 2-32 | 1-15 | Tolclofos-methyl |
| 2-33 | 1-15 | Thiram |
| 2-34 | 1-15 | Captan |
| 2-35 | 1-15 | Carboxin |
| 2-36 | 1-15 | Boscalid |
| 2-37 | 1-15 | Thiabendazole |
| 2-38 | 1-15 | Ethaboxam |
| 2-39 | 1-18 | Pyraclostrobin |
| 2-40 | 1-18 | Azoxystrobin |
| 2-41 | 1-18 | Trifloxystrobin |
| 2-42 | 1-18 | Mandestrobin |
| 2-43 | 1-18 | Metconazole |
| 2-44 | 1-18 | Prothioconazole |
| 2-45 | 1-18 | Triticonazole |
| 2-46 | 1-18 | Tebuconazole |
| 2-47 | 1-18 | Difenoconazole |
| 2-48 | 1-18 | Ipconazole |
| 2-49 | 1-18 | Thiophanate-methyl |
| 2-50 | 1-18 | Fludioxonil |
| 2-51 | 1-18 | Tolclofos-methyl |
| 2-52 | 1-18 | Thiram |
| 2-53 | 1-18 | Captan |
| 2-54 | 1-18 | Carboxin |
| 2-55 | 1-18 | Boscalid |
| 2-56 | 1-18 | Thiabendazole |
| 2-57 | 1-28 | Boscalid |
| 2-58 | 1-28 | Metconazole |
| 2-59 | 1-28 | Ipconazole |
| 2-60 | 1-28 | Triticonazole |
| 2-61 | 1-28 | Tebuconazole |
| 2-62 | 1-28 | Thiabendazole |
| 2-63 | 1-28 | Carboxin |
| 2-64 | 1-28 | Penflufen |
| 2-65 | 1-28 | Sedaxane |
| 2-66 | 1-28 | Fluxapyroxad |
| 2-67 | 1-28 | Fluopyram |
| 2-68 | 1-28 | Thiram |
| 2-69 | 1-221 | Metconazole |
| 2-70 | 1-27 | Ipconazole |
| 2-71 | 1-14 | Compound 2 |
| 2-72 | 1-15 | Compound 2 |
| 2-73 | 1-28 | Compound 2 |
| 2-74 | 1-86 | Fludioxonil |
| 2-75 | 1-87 | Fludioxonil |
| 2-76 | 1-50 | Pyraclostrobin |
| 2-77 | 1-51 | Pyraclostrobin |
| 2-78 | 1-50 | Trifloxystrobin |
| 2-79 | 1-51 | Trifloxystrobin |
| 2-80 | 1-216 | Penflufen |
| 2-81 | 1-4 | *Bacillus firmus* |
| 2-82 | 1-50 | Tebuconazole |
| 2-83 | 1-51 | Tebuconazole |
| 2-84 | 1-40 | Triazoxide |
| 2-85 | 1-50 | Myclobutanil |
| 2-86 | 1-51 | Myclobutanil |

TABLE 3

| Combination No. | Combination of compounds | | |
|---|---|---|---|
| 3-1 | 2-57 | Pyraclostrobin | Mandestrobin |
| 3-2 | 2-57 | Pyraclostrobin | Tolclofos-methyl |
| 3-3 | 2-57 | Pyraclostrobin | Metconazole |
| 3-4 | 2-57 | Pyraclostrobin | Metalaxyl |
| 3-5 | 2-17 | Pyraclostrobin | Metconazole |
| 3-6 | 2-36 | Pyraclostrobin | Metconazole |
| 3-7 | 2-17 | Pyraclostrobin | Mandestrobin |

TABLE 3-continued

| Combination No. | | Combination of compounds | |
|---|---|---|---|
| 3-8 | 2-36 | Pyraclostrobin | Mandestrobin |
| 3-9 | 2-17 | Pyraclostrobin | Tolclofos-methyl |
| 3-10 | 2-36 | Pyraclostrobin | Tolclofos-methyl |
| 3-11 | 2-10 | Thiram | |
| 3-12 | 2-14 | Trifloxystrobin | |
| 3-13 | 2-33 | Trifloxystrobin | |
| 3-14 | 2-24 | Trifloxystrobin | |
| 3-15 | 2-22 | Mandestrobin | |
| 3-16 | 2-23 | Azoxystrobin | |
| 3-17 | 2-23 | Thiabendazole | |
| 3-18 | 2-32 | Trifloxystrobin | |
| 3-19 | 2-32 | Azoxystrobin | |
| 3-20 | 2-32 | Thiabendazole | |
| 3-21 | 2-19 | Trifloxystrobin | Mandestrobin |
| 3-22 | 2-19 | Azoxystrobin | Mandestrobin |
| 3-23 | 2-29 | Thiram | Mandestrobin |
| 3-24 | 2-29 | Tolclofos-methyl | |
| 3-25 | 2-5 | Ethaboxam | Mandestrobin |
| 3-26 | 2-58 | Mandestrobin | |
| 3-27 | 2-58 | Difenoconazole | |
| 3-28 | 2-5 | Difenoconazole | |
| 3-29 | 2-24 | Difenoconazole | |
| 3-30 | 2-59 | Difenoconazole | |
| 3-31 | 2-60 | Difenoconazole | |
| 3-32 | 2-61 | Difenoconazole | |
| 3-33 | 2-62 | Difenoconazole | |
| 3-34 | 2-63 | Difenoconazole | |
| 3-35 | 2-64 | Difenoconazole | |
| 3-36 | 2-65 | Difenoconazole | |
| 3-37 | 2-66 | Difenoconazole | |
| 3-38 | 2-67 | Difenoconazole | |
| 3-39 | 2-68 | Difenoconazole | |
| 3-40 | 2-19 | Metconazole | Difenoconazole |
| 3-41 | 2-19 | Ipconazole | Difenoconazole |
| 3-42 | 2-19 | Triticonazole | Difenoconazole |
| 3-43 | 2-19 | Tebuconazole | Difenoconazole |
| 3-44 | 2-19 | Thiabendazole | Difenoconazole |
| 3-45 | 2-19 | Carboxin | Difenoconazole |
| 3-46 | 2-19 | Penflufen | Difenoconazole |
| 3-47 | 2-19 | Sedaxane | Difenoconazole |
| 3-48 | 2-19 | Fluxapyroxad | Difenoconazole |
| 3-49 | 2-19 | Fluopyram | Difenoconazole |
| 3-50 | 2-19 | Thiram | Difenoconazole |
| 3-51 | 2-17 | Pyraclostrobin | Ipconazole |
| 3-52 | 2-36 | Pyraclostrobin | Ipconazole |
| 3-53 | 2-57 | Pyraclostrobin | Ipconazole |
| 3-54 | 2-10 | Trifloxystrobin | |
| 3-55 | 2-29 | Trifloxystrobin | |
| 3-56 | 2-59 | Trifloxystrobin | |
| 3-57 | 2-19 | Ipconazole | Trifloxystrobin |
| 3-58 | 2-29 | Azoxystrobin | |
| 3-59 | 2-59 | Azoxystrobin | |
| 3-60 | 2-19 | Ipconazole | Azoxystrobin |
| 3-61 | 2-5 | Mandestrobin | Carboxin |
| 3-62 | 2-5 | Mandestrobin | Penflufen |
| 3-63 | 2-5 | Mandestrobin | Sedaxane |
| 3-64 | 2-5 | Mandestrobin | Fluxapyroxad |
| 3-65 | 2-5 | Mandestrobin | Fluopyram |
| 3-66 | 2-5 | Mandestrobin | Oxycarboxin |
| 3-67 | 2-5 | Mandestrobin | Thifluzamide |
| 3-68 | 2-5 | Mandestrobin | Flutolanil |
| 3-69 | 2-5 | Mandestrobin | Pencycuron |
| 3-70 | 2-5 | Mandestrobin | Fludioxonil |
| 3-71 | 2-32 | Mandestrobin | Metconazole |
| 3-72 | 2-32 | Mandestrobin | Tebuconazole |
| 3-73 | 2-32 | Mandestrobin | Difenoconazole |
| 3-74 | 2-32 | Mandestrobin | Triticonazole |
| 3-75 | 2-32 | Mandestrobin | Imazalil |
| 3-76 | 2-32 | Mandestrobin | Triadimenol |
| 3-77 | 2-32 | Mandestrobin | Fluquinconazole |
| 3-78 | 2-32 | Mandestrobin | Prochloraz |
| 3-79 | 2-32 | Mandestrobin | Prothioconazole |
| 3-80 | 2-32 | Mandestrobin | Diniconazole |
| 3-81 | 2-32 | Mandestrobin | Diniconazole M |
| 3-82 | 2-32 | Mandestrobin | Ipconazole |
| 3-83 | 2-32 | Mandestrobin | Cyproconazole |
| 3-84 | 2-32 | Mandestrobin | Tetraconazole |
| 3-85 | 2-32 | Mandestrobin | Carboxin |

TABLE 3-continued

| Combination No. | Combination of compounds | | | |
|---|---|---|---|---|
| 3-86 | 2-32 | Mandestrobin | Penflufen | |
| 3-87 | 2-32 | Mandestrobin | Sedaxane | |
| 3-88 | 2-32 | Mandestrobin | Fluxapyroxad | |
| 3-89 | 2-32 | Mandestrobin | Fluopyram | |
| 3-90 | 2-32 | Mandestrobin | Oxycarboxin | |
| 3-91 | 2-32 | Mandestrobin | Fludioxonil | |
| 3-92 | 2-32 | Mandestrobin | Thiram | |
| 3-93 | 2-32 | Mandestrobin | Captan | |
| 3-94 | 2-32 | Mandestrobin | Thiophanate-methyl | |
| 3-95 | 2-32 | Mandestrobin | Thiabendazole | |
| 3-96 | 2-32 | Mandestrobin | Metconazole | |
| 3-97 | 2-13 | Mandestrobin | Tebuconazole | |
| 3-98 | 2-13 | Mandestrobin | Difenoconazole | |
| 3-99 | 2-13 | Mandestrobin | Triticonazole | |
| 3-100 | 2-13 | Mandestrobin | Imazalil | |
| 3-101 | 2-13 | Mandestrobin | Triadimenol | |
| 3-102 | 2-13 | Mandestrobin | Fluquinconazole | |
| 3-103 | 2-13 | Mandestrobin | Prochloraz | |
| 3-104 | 2-13 | Mandestrobin | Prothioconazole | |
| 3-105 | 2-13 | Mandestrobin | Diniconazole | |
| 3-106 | 2-13 | Mandestrobin | Diniconazole M | |
| 3-107 | 2-13 | Mandestrobin | Ipconazole | |
| 3-108 | 2-13 | Mandestrobin | Cyproconazole | |
| 3-109 | 2-13 | Mandestrobin | Tetraconazole | |
| 3-110 | 2-13 | Mandestrobin | Carboxin | |
| 3-111 | 2-13 | Mandestrobin | Penflufen | |
| 3-112 | 2-13 | Mandestrobin | Sedaxane | |
| 3-113 | 2-13 | Mandestrobin | Fluxapyroxad | |
| 3-114 | 2-13 | Mandestrobin | Fluopyram | |
| 3-115 | 2-13 | Mandestrobin | Oxycarboxin | |
| 3-116 | 2-13 | Mandestrobin | Fludioxonil | |
| 3-117 | 2-13 | Mandestrobin | Thiram | |
| 3-118 | 2-13 | Mandestrobin | Captan | |
| 3-119 | 2-13 | Mandestrobin | Thiophanate-methyl | |
| 3-120 | 2-13 | Mandestrobin | Thiabendazole | |
| 3-121 | 2-69 | Mandestrobin | Oxadixyl | |
| 3-122 | 2-69 | Mandestrobin | Hymexazol | |
| 3-123 | 2-69 | Mandestrobin | Fenamidone | |
| 3-124 | 2-69 | Mandestrobin | Cymoxanil | |
| 3-125 | 2-69 | Mandestrobin | Fluopicolide | |
| 3-126 | 2-70 | Carboxin | | |
| 3-127 | 2-10 | Tolclofos-methyl | Carboxin | |
| 3-128 | 2-10 | Tolclofos-methyl | Penflufen | |
| 3-129 | 2-10 | Tolclofos-methyl | Sedaxane | |
| 3-130 | 2-10 | Tolclofos-methyl | Fluxapyroxad | |
| 3-131 | 2-10 | Tolclofos-methyl | Fluopyram | |
| 3-132 | 2-5 | Tolclofos-methyl | | |
| 3-133 | 2-5 | Tolclofos-methyl | Azoxystrobin | |
| 3-134 | 2-5 | Tolclofos-methyl | Fluoxastrobin | |
| 3-135 | 2-5 | Tolclofos-methyl | Trifloxystrobin | |
| 3-136 | 2-5 | Tolclofos-methyl | Pyraclostrobin | |
| 3-137 | 2-5 | Tolclofos-methyl | Orysastrobin | |
| 3-138 | 2-5 | Tolclofos-methyl | Carboxin | |
| 3-139 | 2-5 | Tolclofos-methyl | Oxycarboxin | |
| 3-140 | 2-5 | Tolclofos-methyl | Fludioxonil | |
| 3-141 | 2-5 | Tolclofos-methyl | Thiram | |
| 3-142 | 2-5 | Tolclofos-methyl | Captan | |
| 3-143 | 2-5 | Tolclofos-methyl | Thiophanate-methyl | |
| 3-144 | 2-5 | Tolclofos-methyl | Thiabendazole | |
| 3-145 | 2-5 | Ethaboxam | | |
| 3-146 | 2-5 | Ethaboxam | Tolclofos-methyl | |
| 3-147 | 2-19 | Tolclofos-methyl | Compound 1 | |
| 3-148 | 2-38 | Metconazole | Compound 1 | |
| 3-149 | 2-38 | Compound 1 | Compound 2 | |
| 3-150 | 2-38 | Compound 1 | Mandestrobin | |
| 3-151 | 2-19 | Ipconazole | Compound 1 | |
| 3-152 | 2-19 | Compound 1 | Compound 2 | |
| 3-153 | 2-19 | Boscalid | Pyraclostrobin | Metconazole |
| 3-154 | 2-19 | Boscalid | Pyraclostrobin | Ipconazole |
| 3-155 | 2-38 | Boscalid | Pyraclostrobin | Metconazole |
| 3-156 | 2-19 | Boscalid | Pyraclostrobin | Mandestrobin |
| 3-157 | 2-38 | Boscalid | Pyraclostrobin | Mandestrobin |
| 3-158 | 2-19 | Boscalid | Pyraclostrobin | Tolclofos-methyl |
| 3-159 | 2-38 | Boscalid | Pyraclostrobin | Tolclofos-methyl |
| 3-160 | 2-32 | Mandestrobin | Metconazole | Oxadixyl |
| 3-161 | 2-32 | Mandestrobin | Metconazole | Hymexazol |
| 3-162 | 2-32 | Mandestrobin | Metconazole | Fenamidone |
| 3-163 | 2-32 | Mandestrobin | Metconazole | Cymoxanil |

TABLE 3-continued

| Combination No. | | Combination of compounds | | |
|---|---|---|---|---|
| 3-164 | 2-32 | Mandestrobin | Metconazole | Fluopicolide |
| 3-165 | 2-13 | Mandestrobin | Metconazole | Oxadixyl |
| 3-166 | 2-13 | Mandestrobin | Metconazole | Hymexazol |
| 3-167 | 2-13 | Mandestrobin | Metconazole | Fenamidone |
| 3-168 | 2-13 | Mandestrobin | Metconazole | Cymoxanil |
| 3-169 | 2-13 | Mandestrobin | Metconazole | Fluopicolide |
| 3-170 | 2-5 | Ethaboxam | Tolclofos-methyl | Azoxystrobin |
| 3-171 | 2-5 | Ethaboxam | Tolclofos-methyl | Fluoxastrobin |
| 3-172 | 2-5 | Ethaboxam | Tolclofos-methyl | Trifloxystrobin |
| 3-173 | 2-5 | Ethaboxam | Tolclofos-methyl | Pyraclostrobin |
| 3-174 | 2-5 | Ethaboxam | Tolclofos-methyl | Orysastrobin |
| 3-175 | 2-5 | Ethaboxam | Tolclofos-methyl | Carboxin |
| 3-176 | 2-5 | Ethaboxam | Tolclofos-methyl | Penflufen |
| 3-177 | 2-5 | Ethaboxam | Tolclofos-methyl | Sedaxane |
| 3-178 | 2-5 | Ethaboxam | Tolclofos-methyl | Fluxapyroxad |
| 3-179 | 2-72 | Metconazole | | |
| 3-180 | 2-71 | Metconazole | | |
| 3-181 | 2-73 | Difenoconazole | | |
| 3-182 | 2-73 | Triticonazole | | |
| 3-183 | 2-73 | Tebuconazole | | |
| 3-184 | 2-73 | Thiabendazole | | |
| 3-185 | 2-73 | Carboxin | | |
| 3-186 | 2-73 | Thiram | | |
| 3-187 | 2-73 | Captan | | |
| 3-188 | 2-71 | Mandestrobin | | |
| 3-189 | 2-72 | Mandestrobin | | |
| 3-190 | 2-73 | Mandestrobin | | |
| 3-191 | 2-71 | Tolclofos-methyl | | |
| 3-192 | 2-72 | Tolclofos-methyl | | |
| 3-193 | 2-71 | Captan | | |
| 3-194 | 2-72 | Captan | | |
| 3-195 | 2-71 | Ethaboxam | Metconazole | |
| 3-196 | 2-71 | Ethaboxam | Mandestrobin | |
| 3-197 | 2-71 | Ethaboxam | Tolclofos-methyl | |
| 3-198 | 2-73 | Tolclofos-methyl | | |
| 3-199 | 2-71 | Ethaboxam | Ipconazole | |
| 3-200 | 2-71 | Ethaboxam | Difenoconazole | |
| 3-201 | 2-71 | Ethaboxam | Triticonazole | |
| 3-202 | 2-71 | Ethaboxam | Tebuconazole | |
| 3-203 | 2-71 | Ethaboxam | Thiabendazole | |
| 3-204 | 2-71 | Ethaboxam | Carboxin | |
| 3-205 | 2-71 | Ethaboxam | Thiram | |
| 3-206 | 2-71 | Ethaboxam | Captan | |
| 3-207 | 2-73 | Ipconazole | | |
| 3-208 | 2-71 | Fludioxonil | Azoxystrobin | Prothioconazole |
| 3-209 | 2-71 | Fludioxonil | Pyraclostrobin | Prothioconazole |
| 3-210 | 2-71 | Fludioxonil | Trifloxystrobin | Prothioconazole |
| 3-211 | 2-71 | Fludioxonil | Fluoxastrobin | Prothioconazole |
| 3-212 | 2-71 | Fludioxonil | Azoxystrobin | Triticonazole |
| 3-213 | 2-71 | Fludioxonil | Pyraclostrobin | Triticonazole |
| 3-214 | 2-71 | Fludioxonil | Trifloxystrobin | Triticonazole |
| 3-215 | 2-71 | Fludioxonil | Fluoxastrobin | Triticonazole |
| 3-216 | 2-71 | Fludioxonil | Azoxystrobin | Tebuconazole |
| 3-217 | 2-71 | Fludioxonil | Pyraclostrobin | Tebuconazole |
| 3-218 | 2-71 | Fludioxonil | Trifloxystrobin | Tebuconazole |
| 3-219 | 2-71 | Fludioxonil | Fluoxastrobin | Tebuconazole |
| 3-220 | 2-71 | Fludioxonil | Azoxystrobin | Difenoconazole |
| 3-221 | 2-71 | Fludioxonil | Pyraclostrobin | Difenoconazole |
| 3-222 | 2-71 | Fludioxonil | Trifloxystrobin | Difenoconazole |
| 3-223 | 2-71 | Fludioxonil | Fluoxastrobin | Difenoconazole |
| 3-224 | 2-72 | Fludioxonil | Azoxystrobin | Prothioconazole |
| 3-225 | 2-72 | Fludioxonil | Pyraclostrobin | Prothioconazole |
| 3-226 | 2-72 | Fludioxonil | Trifloxystrobin | Prothioconazole |
| 3-227 | 2-72 | Fludioxonil | Fluoxastrobin | Prothioconazole |
| 3-228 | 2-72 | Fludioxonil | Azoxystrobin | Triticonazole |
| 3-229 | 2-72 | Fludioxonil | Pyraclostrobin | Triticonazole |
| 3-230 | 2-72 | Fludioxonil | Trifloxystrobin | Triticonazole |
| 3-231 | 2-72 | Fludioxonil | Fluoxastrobin | Triticonazole |
| 3-232 | 2-72 | Fludioxonil | Azoxystrobin | Tebuconazole |
| 3-233 | 2-72 | Fludioxonil | Pyraclostrobin | Tebuconazole |
| 3-234 | 2-72 | Fludioxonil | Trifloxystrobin | Tebuconazole |
| 3-235 | 2-72 | Fludioxonil | Fluoxastrobin | Tebuconazole |
| 3-236 | 2-72 | Fludioxonil | Azoxystrobin | Difenoconazole |
| 3-237 | 2-72 | Fludioxonil | Pyraclostrobin | Difenoconazole |
| 3-238 | 2-72 | Fludioxonil | Trifloxystrobin | Difenoconazole |
| 3-239 | 2-72 | Fludioxonil | Fluoxastrobin | Difenoconazole |
| 3-240 | 2-71 | Mandestrobin | Compound 1 | |
| 3-241 | 2-71 | Pyraclostrobin | Compound 1 | |

TABLE 3-continued

| Combination No. | Combination of compounds | | | |
|---|---|---|---|---|
| 3-242 | 2-71 | Azoxystrobin | Compound 1 | |
| 3-243 | 2-71 | Trifloxystrobin | Compound 1 | |
| 3-244 | 2-71 | Metconazole | Compound 1 | |
| 3-245 | 2-71 | Prothioconazole | Compound 1 | |
| 3-246 | 2-71 | Triticonazole | Compound 1 | |
| 3-247 | 2-71 | Tebuconazole | Compound 1 | |
| 3-248 | 2-71 | Difenoconazole | Compound 1 | |
| 3-249 | 2-71 | Ipconazole | Compound 1 | |
| 3-250 | 2-71 | Thiophanate-methyl | Compound 1 | |
| 3-251 | 2-71 | Fludioxonil | Compound 1 | |
| 3-252 | 2-71 | Tolclofos-methyl | Compound 1 | |
| 3-253 | 2-71 | Thiuram | Compound 1 | |
| 3-254 | 2-71 | Captan | Compound 1 | |
| 3-255 | 2-71 | Carboxin | Compound 1 | |
| 3-256 | 2-71 | Penflufen | Compound 1 | |
| 3-257 | 2-71 | Sedaxane | Compound 1 | |
| 3-258 | 2-71 | Fluxapyroxad | Compound 1 | |
| 3-259 | 2-71 | Fluopyram | Compound 1 | |
| 3-260 | 2-71 | Boscalid | Compound 1 | |
| 3-261 | 2-71 | Thiabendazole | Compound 1 | |
| 3-262 | 2-72 | Mandestrobin | Compound 1 | |
| 3-263 | 2-72 | Pyraclostrobin | Compound 1 | |
| 3-264 | 2-72 | Azoxystrobin | Compound 1 | |
| 3-265 | 2-72 | Trifloxystrobin | Compound 1 | |
| 3-266 | 2-72 | Metconazole | Compound 1 | |
| 3-267 | 2-72 | Prothioconazole | Compound 1 | |
| 3-268 | 2-72 | Triticonazole | Compound 1 | |
| 3-269 | 2-72 | Tebuconazole | Compound 1 | |
| 3-270 | 2-72 | Difenoconazole | Compound 1 | |
| 3-271 | 2-72 | Ipconazole | Compound 1 | |
| 3-272 | 2-72 | Thiophanate-methyl | Compound 1 | |
| 3-273 | 2-72 | Fludioxonil | Compound 1 | |
| 3-274 | 2-72 | Tolclofos-methyl | Compound 1 | |
| 3-275 | 2-72 | Thiuram | Compound 1 | |
| 3-276 | 2-72 | Captan | Compound 1 | |
| 3-277 | 2-72 | Carboxin | Compound 1 | |
| 3-278 | 2-72 | Penflufen | Compound 1 | |
| 3-279 | 2-72 | Sedaxane | Compound 1 | |
| 3-280 | 2-72 | Fluxapyroxad | Compound 1 | |
| 3-281 | 2-72 | Fluopyram | Compound 1 | |
| 3-282 | 2-72 | Boscalid | Compound 1 | |
| 3-283 | 2-72 | Thiabendazole | Compound 1 | |
| 3-284 | 2-74 | Azoxystrobin | Abamectin | Sedaxane |
| 3-285 | 2-75 | Azoxystrobin | Abamectin | Sedaxane |
| 3-286 | 2-76 | Fluxapyroxad | | |
| 3-287 | 2-77 | Fluxapyroxad | | |
| 3-288 | 2-81 | Fluxapyroxad | | |
| 3-289 | 2-78 | Penflufen | | |
| 3-290 | 2-79 | Penflufen | | |
| 3-291 | Fipronil | Pyraclostrobin | Thiophanate-methyl | Fluxapyroxad |
| 3-292 | Fluoxastrobin | Prothioconazole | Tebuconazole | Triazoxide |
| 3-293 | 3-286 | Sedaxane | | |
| 3-294 | 3-287 | Sedaxane | | |
| 3-295 | 2-85 | Trifloxystrobin | Fluxapyroxad | Thiodicarb |
| 3-296 | 2-86 | Trifloxystrobin | Fluxapyroxad | Thiodicarb |
| 3-297 | 2-85 | Pyraclostrobin | Fluxapyroxad | Thiodicarb |
| 3-298 | 2-86 | Pyraclostrobin | Fluxapyroxad | Thiodicarb |

In the present method for controlling harmful organisms, examples of the compound B used to perform a foliage treatment on crops are described below, but the examples are not limited thereto.

Prothioconazole;
Epoxyconazole;
Cyproconazole;
Propiconazole;
Tetraconazole;
Tebuconazole;
Metconazole;
Benzobindiflupyr;
Fluxapyroxad;
Compound 1;
Pyraclostrobin;
Azoxystrobin;
Trifloxystrobin;
Picoxystrobin;
Azoxystrobin+benzobindiflupyr;
Azoxystrobin+propiconazole;
Azoxystrobin+tebuconazole;
Azoxystrobin+flutriafol;
Azoxystrobin+tetraconazole;
Azoxystrobin+cyproconazole;
Prothioconazole+trifloxystrobin;
Pyraclostrobin+fluxapyroxad;
Trifloxystrobin+tebuconazole;
Trifloxystrobin+prothioconazole;
Pyraclostrobin+metconazole;
Pyraclostrobin+epoxyconazole;

Picoxystrobin+cyproconazole;
Compound 1
Compound 1+tebuconazole;
Compound 1+prothioconazole;
F9990;
F9990+tebuconazole; and
F9990+prothioconazole.

In the present invention, all individual combinations of (a) the cultivation area of crops is treated with the compound X alone or treated with a combination of the compound X and a herbicide or a safener exemplified above; (b) the crop seeds are treated with one compound selected from the above-described compound group A alone or treated with a combination listed in Tables 1 to 3; (c) the crops are subjected to a foliage treatment with the compound B exemplified above; and (d) various crops have been described.

In the cultivation of crops of the present invention, it is possible to perform typical plant nutrition management on crop cultivation. The fertilization system may be a system based on Precision Agriculture or a uniform system which has been practically used. Further, nitrogen-fixing bacteria or mycorrhizal fungi may be inoculated to crops together with the seed treatment applied to the crops with the compound group A.

EXAMPLES

Hereinafter, the present invention will be described in detail with reference to examples, but the present invention is not limited thereto.

First, the evaluation criteria of the effects of controlling harmful arthropods, the effects of controlling plant pathogens, the herbicidal effects, and the phytotoxicity on crops, shown in the following examples, will be described.

[Effects of Controlling Harmful Arthropods]

In the evaluation the effects controlling harmful arthropods, the life and death of insects at the time of investigation is determined and the controlling rate is acquired using the following equation.

Controlling rate (%)=100×(1−$T/C$)

Further, the characters in the equation represent the followings.

C: number of insects in an untreated area at the time of observation

T: number of insects in a treated area at the time of observation

[Effects of Controlling Plant Pathogens]

In the evaluation of the effects of controlling plant pathogens, when the symptoms caused by the plant pathogens at the time of investigation are compared to those in an untreated area and there is no difference or almost no difference between the symptoms, this case is evaluated as "0". Further, when there are no symptoms or almost no symptoms caused by the plant pathogens, this case is evaluated as "100". The effects are evaluated on a scale of 0 to 100.

[Herbicidal Effects]

In the evaluation of the herbicidal effects, when the sprouting or growing state of the test weeds at the time of investigation is compared to that of weeds in an untreated area and there is no difference or almost no difference between the states, this case is evaluated as "0". Further, when the test plants are completely withered or sprouting or growing of plants is completely suppressed, this case is evaluated as "100". The effects are evaluated on a scale of 0 to 100.

[Phytotoxicity on Crops]

In the evaluation of phytotoxicity on crops, a case where phytotoxicity is not confirmed is evaluated as "harmless", a case where mild phytotoxicity is confirmed is evaluated as "small", a case where moderate phytotoxicity is confirmed is evaluated as "medium", and a case where strong phytotoxicity is confirmed is evaluated as "large".

When crop seeds are treated with any combination selected from the combinations listed in Tables 1 to 3 and the cultivation area of the crops is treated with the compound X according to the following method, it is confirmed that the herbicidal effects, the effects of controlling harmful arthropods, and/or the effects of controlling plant pathogens are excellent and the phytotoxicity on the crops is to pose little problem.

Example 1

Soybean seeds (product, Genuity RoundupReady2Yield soybeans) are treated with NipsIt (600 g/L of clothianidin, manufactured by Valent) such that the application rate of NipSIt is set to 206 mL/kg seeds (1.28 fluidounce/100 poundseeds). A formulation containing the compound X (an emulsion (hereinafter, referred to as a formulation X) obtained by sufficiently mixing 5 parts by weight of the compound X, 2 parts by weight of Geronol FF/4-E (manufactured by Rhodia Inc.), 8 parts by weight of Geronol FF/6-E (manufactured by Rhodia Inc.), and 85 parts by weight of Solvesso 200 (manufactured by Exxon Mobile Corporation)) is diluted with water and a field before sowing the soybeans is treated such that the application rate of the compound X is set to 5, 20, or 80 g/ha. The soybeans are sowed in the field after 7 days from the treatment with the compound X and then the fields are treated such that the application rate of RoundupWeatherMax (660 g/L of glyphosate potassium salt, manufactured by Monsanto Company) is set to 2.338 L/ha (32 fluidounce/acre) at the 3-leaf stage of soybean leaves.

Example 2

Soybean seeds are treated with NipsIt in the same manner as in Example 1. A field before sowing the soybeans is treated with the formulation X and RoundupWeatherMax (660 g/L of glyphosate potassium salt, manufactured by Monsanto Company) such that the application rate of the compound X is set to 5, 20, or 80 g/ha and the application rate of RoundupWeatherMax is set to 2.338 L/ha (32 fluidounce/acre), and the soybeans are sowed in the field after 7 days from the treatment. The fields are treated such that the application rate of RoundupWeatherMax (660 g/L of glyphosate potassium salt, manufactured by Monsanto Company) is set to 2.338 L/ha (32 fluidounce/acre) at the 3-leaf stage of soybean leaves.

Example 3

Soybean seeds are treated with NipsIt in the same manner as in Example 1 and then sowed in a field. On the day following the day of sowing, the field is treated with the formulation X such that the application rate of the compound X is set to 5, 20, or 80 g/ha. The fields are treated such that the application rate of RoundupWeatherMax (660 g/L of glyphosate potassium salt, manufactured by Monsanto Company) is set to 2.338 L/ha (32 fluidounce/acre) at the 3-leaf stage of soybean leaves.

Example 4

Soybean seeds are treated with NipsIt in the same manner as in Example 1 and then sowed in a field. On the day following the day of sowing, the field is treated with the formulation X and RoundupWeatherMax (660 g/L of glyphosate potassium salt, manufactured by Monsanto Company) such that the application rate of the compound X is set to 5, 20, or 80 g/ha and the application rate of RoundupWeatherMax is set to 2.338 L/ha (32 fluidounce/acre). The fields are treated such that the application rate of RoundupWeatherMax (660 g/L, of glyphosate potassium salt, manufactured by Monsanto Company) is set to 2.338 L/ha (32 fluidounce/acre) at the 3-leaf stage of soybean leaves.

Examples 5 to 8

The fields are treated with the formulation X and ValorSX, instead of treating the fields with the formulation X in each of Examples 1 to 4, such that the application rate of the compound X is set to 5, 20, or 80 g/ha and the application rate of ValorSX (51% of flumioxazin, manufactured by Valent) is set to 210 g/ha.

Examples 9 to 12

The fields are treated with ValorXLT (30% of flumioxazin+10.3% of chlorimuron-ethyl, manufactured by Valent), instead of ValorSX, in each of Examples 5 to 8, such that the application rate of ValorXLT is set to 315 g/ha.

Examples 13 to 24

The seeds are treated with INOVATE (160 g/L of clothianidin+13 g/L of metalaxyl+8 g/L of ipconazole, manufactured by Valent), instead of NipsIt in each of Examples 1 to 12, such that the application rate of INOVATE is set to 309 mL/100 kg seeds (4.74 fluid ounce/100 pound seeds).

Examples 25 to 36

The seeds are treated with CruiserMAXX Vibrance (240 g/L of thiamethoxam+36 g/L of metalaxyl M+12 g/L of fludioxonil+12 g/L of sedaxane, manufactured by Syngenta Corporation), instead of NipsIt in each of Examples 1 to 12, such that the application rate of CruiserMAXX Vibrance is set to 235 mL/100 kg seeds (3.22 fluid ounce/100 pound seeds).

Examples 37 to 48

The seeds are treated with Acceleron system (31 mL/100 kg seeds of DX-612 (326 g/L of fluxapyroxad, manufactured by Monsanto Company), 242 mL/100 kg seeds (1.5 fluid ounce/100 pound seeds) of DX-309 (313 g/L of metalaxyl, manufactured by Monsanto Company), 242 mL/100 kg seeds (1.5 fluid ounce/100 pound seeds) of DX-109 (200 g/L of pyraclostrobin, manufactured by Monsanto Company), and 515 mL/100 kg seeds (3.2 fluid ounce/100 pound seeds) of IX-104 (600 g/L of imidacloprid, manufactured by Monsanto Company)) instead of treating the soybean seeds with NipsIt in each of Examples 1 to 12.

Examples 49 to 96

The seeds are subjected to a foliage treatment with the compound 1 in a blooming period of soybeans such that the application rate of the compound 1 is set to 30 g/ha in each of Examples 1 to 48.

Examples 97 to 144

The seeds are subjected to a foliage treatment with the compound 1 and tebuconazole in a blooming period of soybeans such that the application rate of the compound 1 is set to 30 g/ha and the application rate of tebuconazole is set to 150/ha in each of Examples 1 to 48.

Examples 145 to 288

The fields are treated with the formulation X and RoundupWeatherMax (660 g/L of glyphosate potassium salt, manufactured by Monsanto Company), instead of treating the fields with RoundupWeatherMax at the 3-leaf stage of soybean leaves in each of Examples 1 to 144, such that the application rate of the compound X is set to 5, 20, or 80 g/ha and the application rate of RoundupWeatherMax is set to 2.338 L/ha (32 fluid ounce/acre).

Examples 289 to 576

The fields are treated at the 6-leaf stage of soybean leaves instead of the 3-leaf stage of soybean leaves in each of Examples 1 to 288.

Examples 577 to 1152

Corn seeds or cotton seeds are used instead of the soybean seeds in each of Examples 1 to 576.

In Examples 1 to 1152 described above, it is confirmed that the herbicidal effects, the effects of controlling harmful arthropods, and/or the effects of controlling plant pathogens are excellent and the phytotoxicity on the crops is to pose little problem.

INDUSTRIAL APPLICABILITY

According to the method for controlling harmful organisms of the present invention, it is possible to efficiently control harmful organisms in a cultivation area of crops.

The invention claimed is:
1. An herbicidal composition comprising ethyl [3-[2-chloro-4-fluoro-5-(1-methyl-6-trifluoromethyl-2,4-dioxo-1,2,3,4-tetrahydropyrimidin-3-yl)phenoxy]-2-pyridyl oxy]acetate and flumioxazin at a weight ratio of from 1:1 to 1:10.
2. A method for controlling weeds in a crop cultivation area where the crop is sown, the method comprising applying ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate and flumioxazin jointly or separately in any order at a weight ratio of from 1:1 to 1:10.

* * * * *